Figure 1:
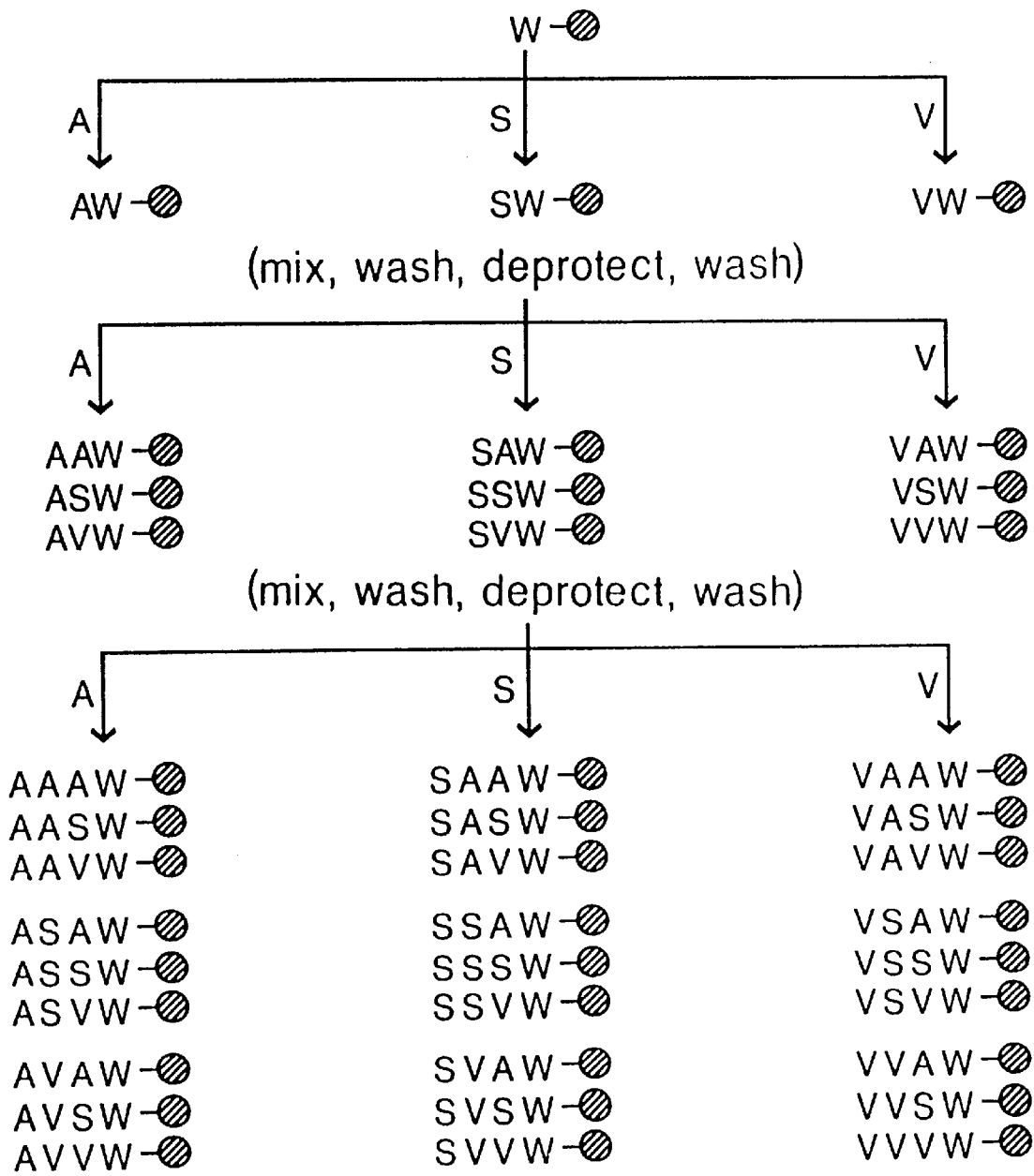

United States Patent [19]
Lam et al.

[11] Patent Number: 5,858,670
[45] Date of Patent: *Jan. 12, 1999

[54] BIO-OLIGOMER LIBRARIES AND A METHOD OF USE THEREOF

[75] Inventors: Kit Sang Lam; Sydney E. Salmon, both of Tucson, Ariz.

[73] Assignee: The Arizona Board of Regents, Tucson, Ariz.

[*] Notice: The term of this patent shall not extend beyond the expiration date of Pat. No. 5,510,240.

[21] Appl. No.: 735,623

[22] Filed: Oct. 23, 1996

Related U.S. Application Data

[63] Continuation of Ser. No. 717,454, Jun. 19, 1991, Pat. No. 5,650,489, which is a continuation-in-part of Ser. No. 546,845, Jul. 2, 1990, abandoned.

[51] Int. Cl.⁶ .......................... C12Q 1/68; G01N 33/566; C12N 15/00
[52] U.S. Cl. .............................. 435/6; 435/7.1; 435/91.1; 436/501; 530/300; 536/23.1
[58] Field of Search .................................. 435/6, 7.1, 7.5, 435/7.92, 91.1; 436/501, 523, 524, 531; 530/300, 322, 333, 335, 344, 387.1; 536/23.1, 24.3, 24.33, 25.3; 935/77, 5, 17

[56] References Cited

U.S. PATENT DOCUMENTS

| | | | |
|---|---|---|---|
| 4,392,997 | 7/1983 | Goldberg | 260/112.5 R |
| 4,555,101 | 11/1985 | Hopp | 260/112.5 R |
| 4,569,792 | 2/1986 | Frank et al. | 260/112.5 R |
| 4,590,003 | 5/1986 | Twardzik et al. | 530/330 |
| 4,618,598 | 10/1986 | Conn | 514/6 |
| 4,625,014 | 11/1986 | Senter et al. | 530/300 |
| 4,631,211 | 12/1986 | Houghten | 428/35 |
| 4,703,008 | 10/1987 | Lin | 435/240.2 |
| 4,705,777 | 11/1987 | Lehrer | 514/12 |
| 4,780,421 | 10/1988 | Kameda et al. | 436/518 |
| 4,784,685 | 11/1988 | Meister | 71/106 |
| 4,798,787 | 1/1989 | McCormic et al. | 435/7 |
| 4,833,072 | 5/1989 | Krchnak et al. | 435/5 |
| 4,833,092 | 5/1989 | Geysen | 436/501 |
| 4,837,304 | 6/1989 | Garsky et al. | 530/328 |
| 4,863,857 | 9/1989 | Blalock | 435/68 |
| 4,988,625 | 1/1991 | Marburg et al. | 436/5 |
| 5,010,175 | 4/1991 | Rutter et al. | 530/334 |
| 5,182,366 | 1/1993 | Huebner et al. | 530/334 |
| 5,194,392 | 3/1993 | Geysen | 436/518 |
| 5,510,240 | 4/1996 | Lam et al. | 435/7.1 |

FOREIGN PATENT DOCUMENTS

| | | | |
|---|---|---|---|
| 0383620A2 | 8/1990 | European Pat. Off. | C12N 15/00 |
| WO 86/00991 | 2/1986 | WIPO | G01N 33/53 |
| WO 86/06487 | 11/1986 | WIPO | G01N 33/53 |
| WO 89/03430 | 4/1989 | WIPO | C12Q 1/00 |
| WO 89/09088 | 10/1989 | WIPO | B01D 15/08 |

OTHER PUBLICATIONS

Furka et al., 14th International Congress of Biochemistry, vol. 5, Abstract FR:013, 1989.
Rand et al., 1989, Abstract only, PNAS 56(74):9657–9661.
Lu et al., 1988, Abstract only, Acta Pharmaceutica Sinica 23(7):564–670.
Brooks et al., 1988, Abstract only, J. Pharmacol. Exp. Ther. (USA) 245/1:211–215.
Breslow et al., 1988, Abstract only, Tetrahedron 44(17):5515–5524.
Furka et al., 1988, More Peptides by Less Labor, European Federation of Medicinal Chemistry, Abstract, Xth International Symposium on Medicinal Chemistry, Budapest, Hungary (Aug. 15–19, 1988) 288:P–168.
Furka et al., 1988, 14th International Congress of Biochemistry, vol. 5, Abstract FR:013.
Geysen et al., 1984, Proc. Natl. Acad. Sci. U.S.A. 81:3998–4002.
Geysen, 1985, Immunol. Today 6:364–369.
Geysen et al., 1986, Mol. Immunol. 102:709–715.
Geysen et al., 1986, Synthetic peptides as antigens, CIBA Foundation Symposium 119, Wiley, Chichester, pp. 130–149.
Geysen et al., 1987, J. Immunol. Meth. 102:259–274.
Geysen et al., 1988, in Peptides, Chemistry and Biology, Proceedings of the Tenth American Peptide Symposium, Marshal, Ed., Escom, pp. 519–523.
Houghten, 1985, Proc. Natl. Acad. Sci. U.S.A. 82:5131–5135.
Krchnak et al., 1989, Int. J. Peptide Protein Res. 33:209–213.
Berg et al., 1989, J. Am. Chem. Soc. 111:8024–8026.
Merrifield, 1985, Angewandte Chemie 24:799–810.
Kauver et al., 1990, BioTechniques 8:204–209.
Kennedy et al., 1987, J. Biol. Chem. 262:5769–5774.
Syu and Kahan, 1989, J. Immunol. Methods 118:153–160.
Zee et al., 1989, Eur. J. Immunol. 19:43–47.
Bost and Blalock, 1989, Meth. Enzym. 168:16–28.
Bost, et al., 1985, Proc. Natl. Acad. Sci. U.S.A. 82:1372–1375.

(List continued on next page.)

*Primary Examiner*—Bradley L. Sisson
*Attorney, Agent, or Firm*—Pennie & Edmonds LLP

[57] ABSTRACT

The instant invention provides a library of bio-oligomers of defined size and known composition, in which the library contains all of the possible sequences of the bio-oligomers, and a method of synthesis thereof. The bio-oligomers of the library may be peptides, nucleic acids, or a combination of the foregoing. The instant invention also provides methods to identify bio-oligomers from a library that demonstrate desired characteristics such as binding, bioactivity and catalytic activity. Thus the instant invention provides a unique and powerful method to identify a useful bio-oligomer sequences from a library more quickly than current state-of-the-art technology allows. Effector molecules for use in treatment or diagnosis of disease are also provided.

13 Claims, 8 Drawing Sheets

OTHER PUBLICATIONS

Blalock and Bost, 1986, Biochem. J. 234:679–683.

Lebl and Eichler, 1989, Peptide Res. 2:297–300.

Furka et al., 1991, General Method For Rapid Synthesis Of Multicomponent Peptide Mixtures, Int. J. Peptide Protein Res. 37:487–493.

Wade et al., 1990, All–D Amino Acid–Containing Channel–Forming Antibiotic Peptides, Proc. Natl. Acad. Sci. 87:4761–4765.

Baum, 1991, Technique Offers Parallel Synthesis Of Thousands Of Chemical Compounds, C&EN, Feb. 25, 1991, pp. 21–22.

Fodor et al., 1991, Light–Directed, Spatially Addresable Parallel Chemical Synthesis, Science 251:767–773.

McCafferty et al., 1990, Phage Antibodies: Filamentous Phage Displaying Antibody Variable Domains, Nature 348:552–554.

Blackwell and Weintraub, 1990, Differences And Similarities In DNA–Binding Preferences Of MyoD And E2A Protein Complexes Revealed By Binding Site Selection, Science 250:1104–1110.

Beardsley, 1990, New Order: Artificial Evolution Creates Proteins Nature Missed, Scientific American, Oct. 1990, 18–24.

Green et al., 1990, In Vitro Genetic Analysis Of The Tetrahymena Self–Splicing Intron, Nature 347:406–408.

Elington and Szotak, 1990, In Vitro Selection Of RNA Molecules That Bind Specific Ligands, Nature 346:818–822.

Cwirla et al., 1990, Peptides On Phage: A Vast Library Of Peptides For Identifying Ligands, Proc. Natl. Acad. Sci. USA 87:6378–6382.

Abelson, 1990, Directed Evolution Of Nucleic Acids By Independent Replication And Selection, Science 249:488–489.

Tuerk and Gold, 1990, Systemic Evolution Of Ligands By Exponential Enrichment: RNA Ligands To Bacteriophage T4 DNA Polymerase, Science 249:505–510.

Devlin et al., 1990, Random Peptide Libraries:A Source Of Specific Protein Binding Molecules, Science 249:404–406.

Scott and Smith, 1990, Searching For Peptide Ligands With An Epitope Library, Science 249:386–390.

Parmley and Smith, 1988, Antibody–Selectable Filamentous Fd Phage Vectors: Affinity Purification Of Target Genes, Gene 73:305–318.

BIO-OLIGOMER LIBRARIES AND A METHOD OF USE THEREOF

This application is a continuation of application Ser. No. 07/717,454 filed Jun. 19, 1991, now U.S. Pat. No. 5,650,489, which, in turn, is a continuation-in-part of application Ser. No. 07/546,845 filed Jul. 2, 1990, currently abandoned.

1. FIELD OF THE INVENTION

The invention relates to a library of bio-oligomers attached to solid phase supports wherein each solid phase support is attached to a single bio-oligomer species and all possible combinations of monomer subunits of which the bio-oligomers are composed are included in this library. The bio-oligomer of the invention may be a peptide, an oligonucleotide or a chimeric peptide-oligonucleotide construct. The invention also relates to a method for synthesizing such a library. The invention also relates to the use of the bio-oligomers of the library to identify and characterize ligands capable of binding an acceptor molecule or mediating a biological activity of interest. The bio-oligomers of the library may also catalyze a chemical reaction.

2. BACKGROUND OF THE INVENTION

Recognition and binding of ligands regulate almost all biological processes, such as immune recognition, cell signalling and communication, transcription and translation, intracellular signalling, and catalysis, i.e., enzyme reactions. There is a longstanding interest in the art to identify molecules which act as agonists or which can agonize or antagonize the activity of ligands such as hormones, growth factors, and neurotransmitters; which induce B-cell (antibody-mediated) or T-cell (cell-mediated) immunity; which can catalyze chemical reactions; or which can regulate gene expression at the level of transcription or translation.

Of particular interest are protein or peptide ligands. These comprise the majority of hormones, growth factors, neuroactive molecules, and immune epitopes. Furthermore, as discussed infra, most efforts at creating antagonists or agonists of receptor-mediated biological activity, or antibody or T-cell epitopes, have centered on peptides. The development of pharmaceutical agents keyed to the receptor binding sites, however, has been greatly hampered by the difficulty in determining the sequence of the peptide ligands. The sheer number and variety-of such peptide sequences has made this an unattainable goal on any basis except by laboriously isolating a specific complex, identifying the location of the epitope, and sequencing that epitope. The problem is further complicated by the fact that often the epitope consists of amino acid residues that are not contiguous in the primary sequence.

Some researchers in the field have attempted to circumvent this time-consuming process by determining the amino acid sequence of a protein based on the nucleotide sequence of its complement. Proteins are large peptides composed of amino acids; each amino acid is encoded by one or more codons of three nucleic acid residues. For example, peptide A, containing the amino acid glutamine, would be encoded by a codon of the three nucleic acid residues: cytosine, adenine and guanine. The complement to this codon would be guanine (which binds to cytosine), thymine (which binds to adenine) and cytosine and it would code for an amino acid in peptide B. According to the complementarity theory, peptide B would bind to peptide A. In particular, Bost and Blalock (1989, Methods in Enzymology 168:16–28) have suggested that any given peptide will bind to another peptide that is encoded by a complementary sequence of nucleic acid residues and, with this information, have predicted the amino acid sequence of a complementary peptide. They have used the sequence to synthesize a peptide and to test its ability to bind.

This approach did not provide the solution to the problem, however, because the affinity of binding between the complementary peptides was generally very low and required complementary peptides larger than 15 residues. Moreover, this approach requires knowledge of either the amino acid sequence or the nucleic acid sequence of the binding partner of a protein of interest. Furthermore, this approach will not work for epitopes that consist of amino acid residues that are not contiguous in the primary sequence.

Recently, there have been several reports on the preparation of peptide libraries and their use in identifying peptide ligands that can bind to acceptors. One approach uses recombinant bacteriophage to produce large libraries. Using the "phage method" (Scott and Smith, 1990, Science 249:386–390; Cwirla, et al., 1990, Proc. Natl. Acad. Sci., 87:6378–6382; Devlin et al., 1990, Science, 249:404–406), very large libraries can be constructed ($10^6$–$10^8$ chemical entities), but the genetic code and the biological system imposes severe inherent limitations on the versality and diversity of the system. A second approach uses primarily chemical methods, of which the Geysen method (Geysen et al., 1986, Molecular Immunology 23:709–715; Geysen et al. 1987, J. Immunologic Method 102:259–274) and the recent method of Fodor et al. (1991, Science 251, 767–773) are examples. The methodology of Geysen et al. provides for a limited number of peptides ($10^3$–$10^4$) can be synthesized on polyethylene pins in a few days. The method of Fodor et al. utilizes a "light-directed spatially addressable parallel chemical synthesis" technique. This technique is also limited by the relative lack of-development of photochemical peptide synthesis methods.

Large scale parallel concurrent peptide synthesis techniques have also been developed. Houghton reported synthesizing hundreds of analogous peptides simultaneously in polypropylene mesh packets (tea bag method) (Houghton, 1985, Proc. Natl. Acad. Sci U.S.A. 82:5131–5135). Berg et al. (1989, J. Am. Chem. Soc. 111:8024–8026) reported a novel polystyrene-grafted polyethylene film support that is suitable for peptide synthesis in parallel fashion. Both techniques used standard Boc amino acid resin with the standard deprotecting, neutralization, coupling and wash protocols of the original solid phase procedure of Merrifield (1963, J. Am. Chem. Soc. 85:2149–2154).

Furka et al. (1988, 14th International Congress of Biochemistry, Volume 5, Abstract FR:013) described a method to produce a mixture of peptides by separately coupling each of three different amino acids, then mixing all of the resin. The procedure described by Furka et al. provides no satisfactory method to isolate a peptide of interest from the plurality of peptides produced.

Although useful, as a practical matter the chemical techniques of Geysen, Fodor, Houghton, Berg and Furka and co-workers allow the synthesis and testing of only hundreds to a few thousand peptides at a time. These techniques are quite limited in light of the millions of possible peptide sequences, one or more of which might correspond to the binding sites between the entities of interest. With 20 known common amino acids, in any sequence of five amino acids, there are $20^5$, or about $3.2 \times 10^6$, possible amino acid combinations. None of the procedures enable the synthesis of this many peptides at one time. Further multiplicity results by varying peptide chain length. Similarly, conventional peptide synthesis, such as that described in Stewart and Young (1984, Solid Phase Synthesis, Second Edition, Pierce Chemical Co., Rockford, Ill.) does not provide a method for the synthesis of thousands to millions of peptides at a time.

In addition, none of the other conventional peptide synthesis methods provide for the synthesis of a library of peptides bound to solid phase support that is truly random. A truly random peptide library is one with a good statistical distribution of all the molecular species such that the library contains approximately equimolar ratios of all individual species of peptides.

The synthesis of a truly random peptide generally cannot be accomplished by simultaneously adding various amino acids into a single reaction vessel because the coupling rates for various amino acids differs tremendously during solid phase peptide synthesis (SPPS) (Ragnarsson et al., 1971, Acta Chem. Scand. 25:1487, 1489; Ragnarsson et al., 1974, J. Org. Chem. 39:3837–3842). For example, the coupling rate of Fmoc-glycine to a growing peptide is much faster than that of Fmoc-valine, probably due to steric hindrance from the bulky side chain of valine. If one were to mix all 20 activated eukaryotic L-amino acids with the resin during each cycle of coupling, the most rapidly reacting amino acids would be preferentially incorporated into the peptide, and equimolar ratios of each peptide species would not be obtained. Furthermore, each of the possible nucleophiles will have different reactivities.

In addition, none of the prior peptide synthesis methods provides for the synthesis of a library of greater than $10^5$ peptides in which a single peptide species attached to a single solid phase support. The representation of only one species on a support would greatly enhance current techniques for isolating peptides.

Thus, there is a need in the art for a library of truly random peptide sequences, and oligonucleotide sequences, i.e., bio-oligomer sequences in which a single bio-oligomer species can be readily and quickly isolated from the rest of the library. There is also a need in the art for a method for quickly and inexpensively synthesizing thousands to millions of these truly random bio-oligomer sequences.

3. SUMMARY OF THE INVENTION

The present invention is directed to a library of bio-oligomers comprising all possible combinations of subunits, methods of generating the library, and a method of use of the library.

In particular, the present invention provides a method for generating the library comprising repeating the steps of providing at least two aliquots of a solid phase support; separately introducing a set of subunits to the aliquots of the solid phase support; completely coupling the subunit to substantially all sites of the solid phase support to form a solid phase support/new subunit combination, assessing the completeness of coupling and if necessary, forcing the reaction to completeness; thoroughly mixing the aliquots of solid phase support/new subunit combination; and, after repeating the foregoing steps the desired number of times, removing protecting groups such that the bio-oligomer remains linked to the solid phase support. In one embodiment, the subunit may be an amino acid, and the bio-oligomer may be a peptide. In another embodiment, the subunit may be a nucleoside and the bio-oligomer may be an oligonucleotide. In a further embodiment, the nucleoside is deoxyribonucleic acid; in yet another embodiment, the nucleoside is ribonucleic acid. In a further embodiment, the subunit may be an amino acid or a nucleoside, and the bio-oligomer may be a peptide-oligonucleotide chimera.

The present invention provides a method for determining the sequence of a bio-oligomer ligand for an acceptor molecule comprising the steps of generating a random library of bio-oligomer attached to solid phase supports wherein each solid phase support is attached to a single bio-oligomer species and all possible combinations of monomer subunits of which the bio-oligomers are composed are included in the collection; introducing to the random library, an acceptor molecule or substrate molecule of interest such that said acceptor molecule will recognize and bind one or more solid phase support/bio-oligomer species within the library or said substrate molecule will undergo a chemical reaction catalyzed by one or more solid phase support/bio-oligomer species within the library; isolating a solid phase support/bio-oligomer combination that exhibits the desired property; and sequencing the bio-oligomer of the isolated solid phase support/bio-oligomer. In a different embodiment, a portion of the bio-oligomer is released from the solid phase support/bio-oligomer combination in situ and a biological activity of interest is detected in situ. In one embodiment the bio-oligomer is a peptide. In another embodiment, the bio-oligomer is an oligonucleotide, in particular DNA or RNA. In yet a further embodiment, the bio-oligomer is a chimeric peptide/oligonucleotide.

The present invention further provides therapeutic and diagnostic agents comprising bio-oligomer sequences determined according to the foregoing methods.

4. BRIEF DESCRIPTION OF THE DRAWINGS

FIG. 1. Scheme for random peptide synthesis using the split synthesis method for a random tripeptide with a terminal tryptophan added: X-X-X-W (wherein X=S, A, or V; there are $3^3$, or 27, possibilities).

Figure 2:
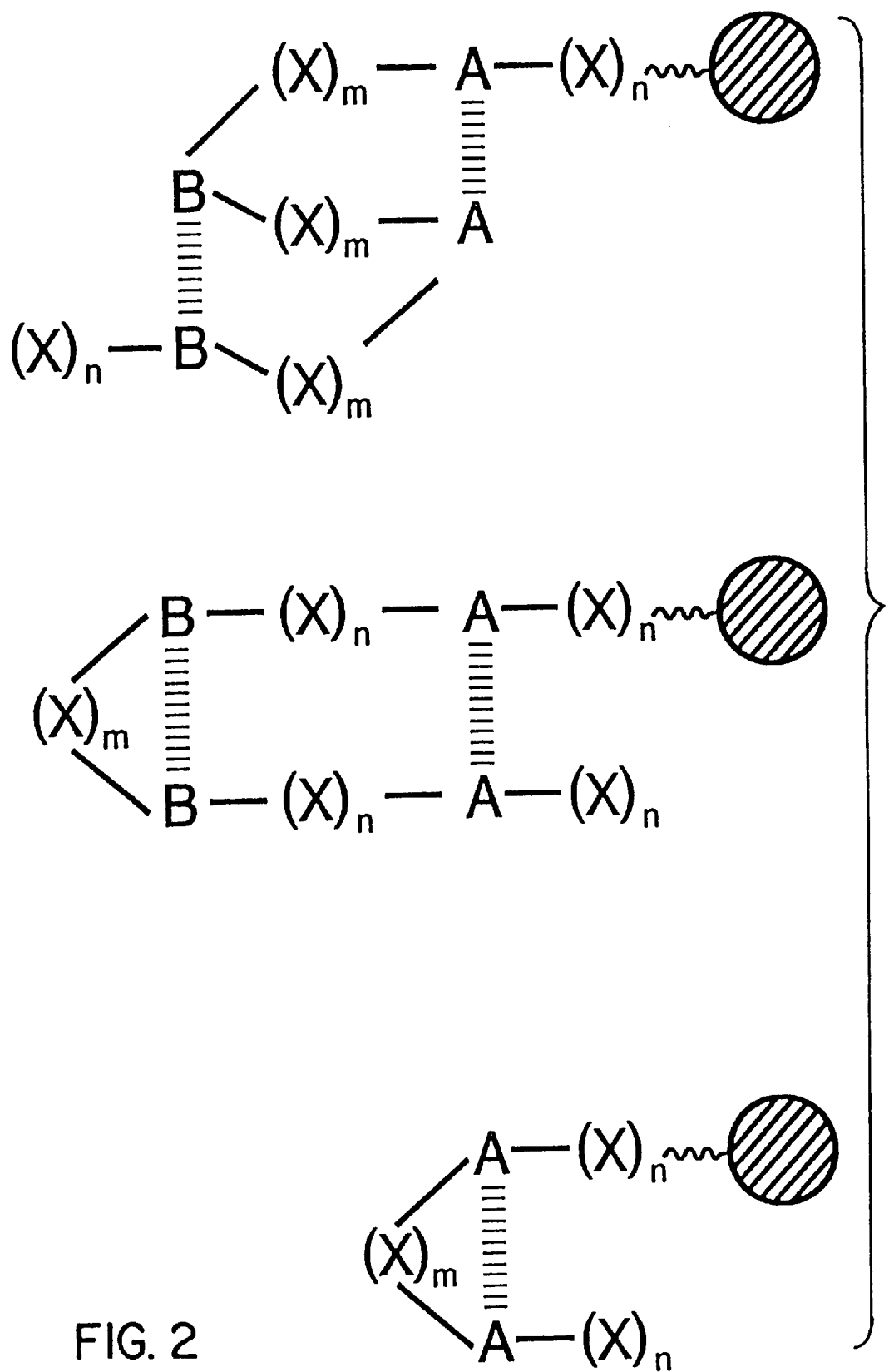

FIG. 2. Schematic drawings of cyclic peptides. n=0, 1, 2, 3, . . . , and m=1, 2, 3, . . . ; n and m may be equivalent, but need not be. Solid lines indicate bonds of the linear peptide; broken lines indicate crosslinks. Pairs of specifically cross-linkable subunits are indicated by A and B. A only crosslinks with A, B only crosslinks with B. (a) "Basket" motif; (b) "ladder" motif; (c) "lariat" motif.

Figure 3:
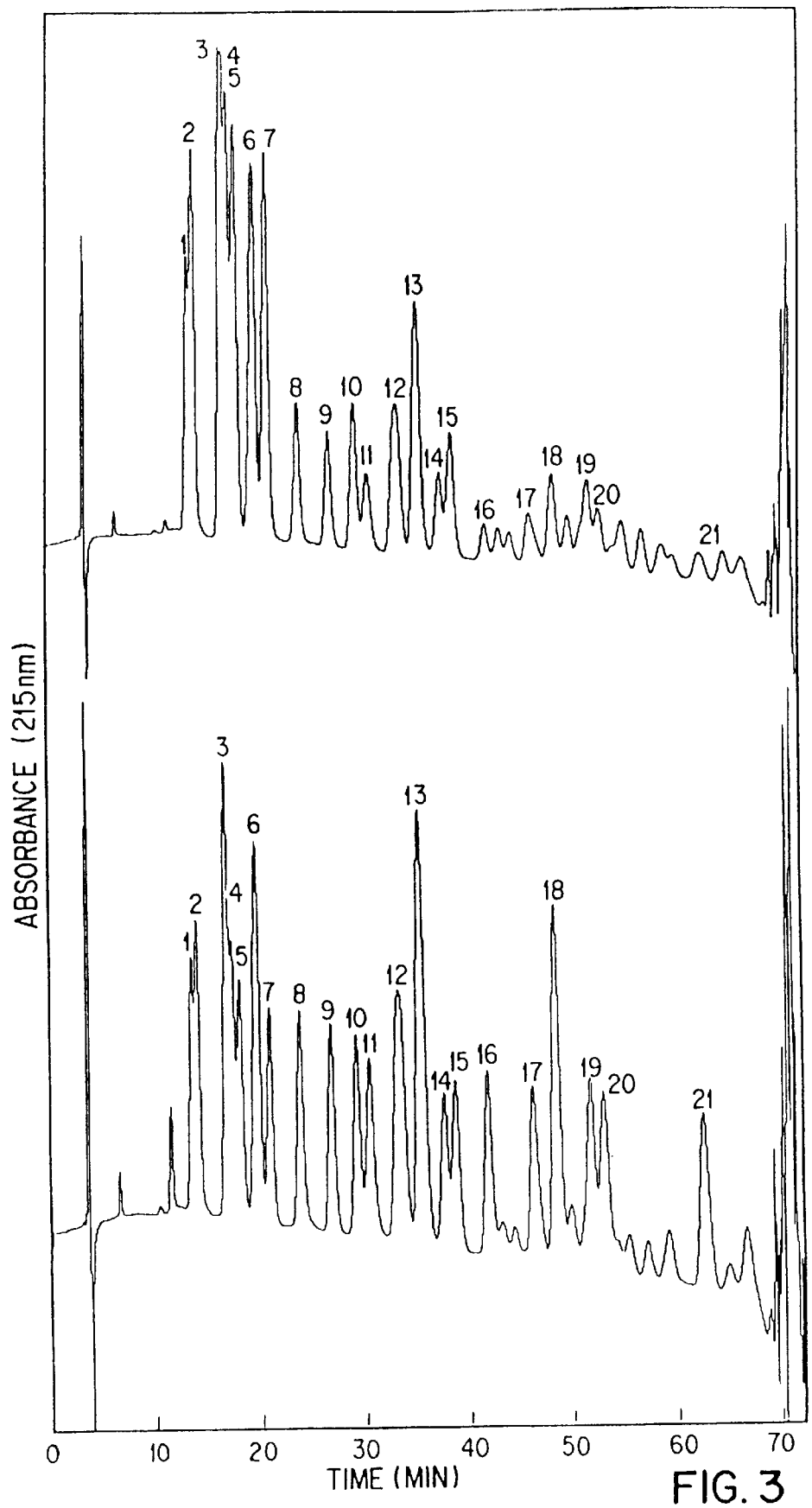

FIG. 3. Chromatograms ($C_{18}$ reverse phase HPLC, Vydac) of random tetrapeptides (X-X-X-W where X=S, A, or V) synthesized by: (A) new approach (see text), and (B) standard solid phase peptide synthesis. The chromatogram was obtained by eluting the column with a linear gradient of acetonitrile. Solvent A: 0.1% trifluoracetic acid and 5% acetonitrile; solvent B: 0.1% trifluoracetic acid and 100% acetonitrile.

Figure 4:
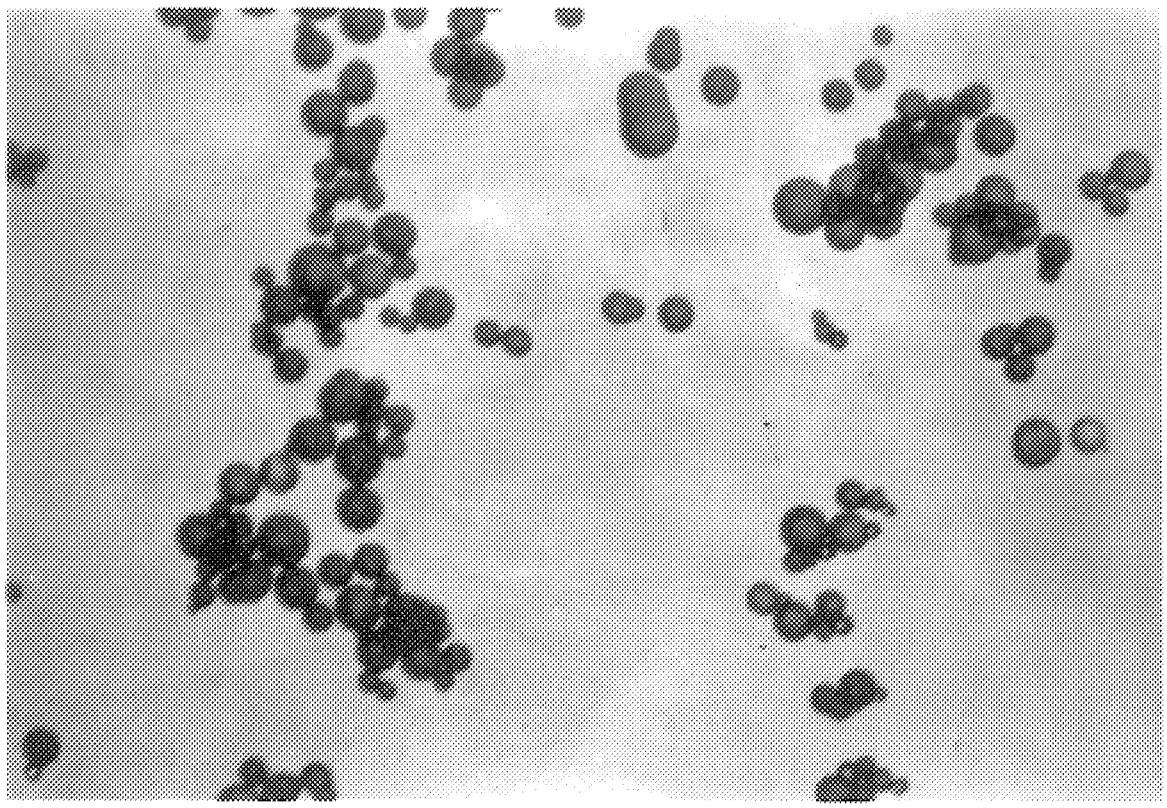

FIG. 4. Photograph of "long v-mos" peptide/beads labeled with the anti-v-mos antibody and a secondary antibody.

Figure 5:
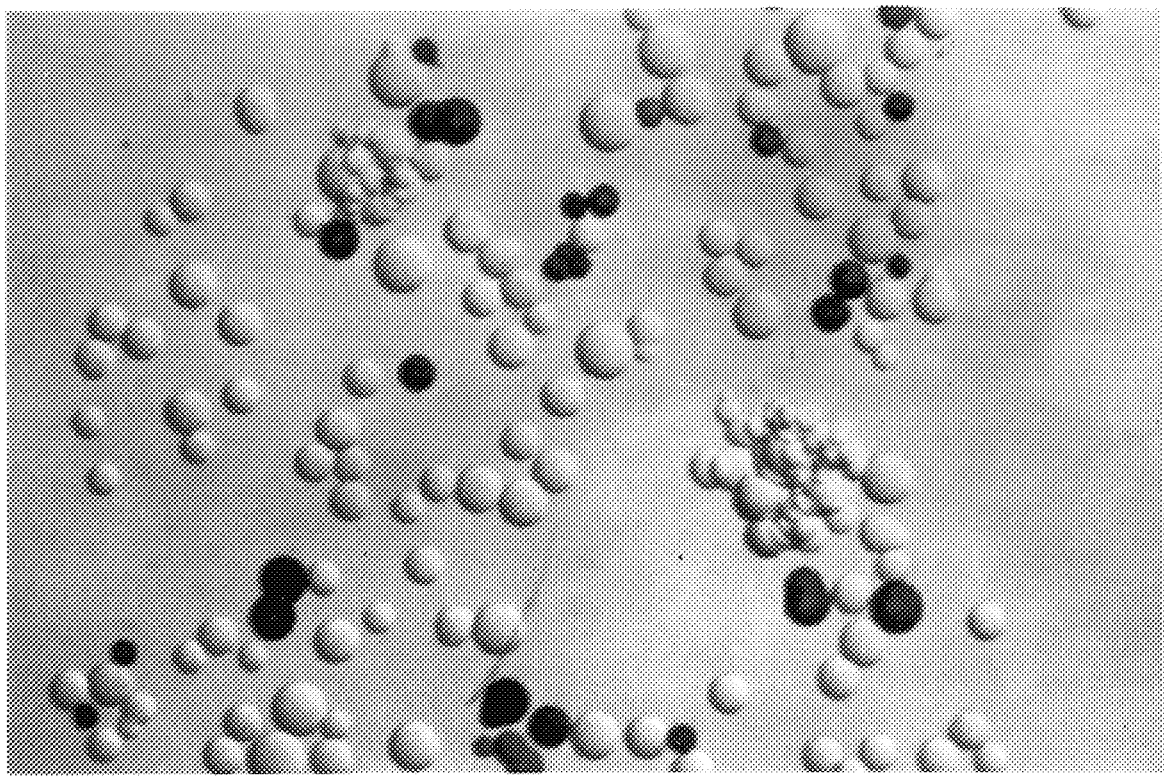

FIG. 5. Photograph of a mixture of "long v-mos" beads and "short v-mos" beads labeled with the anti-v-mos antibody and a secondary antibody.

Figure 6:
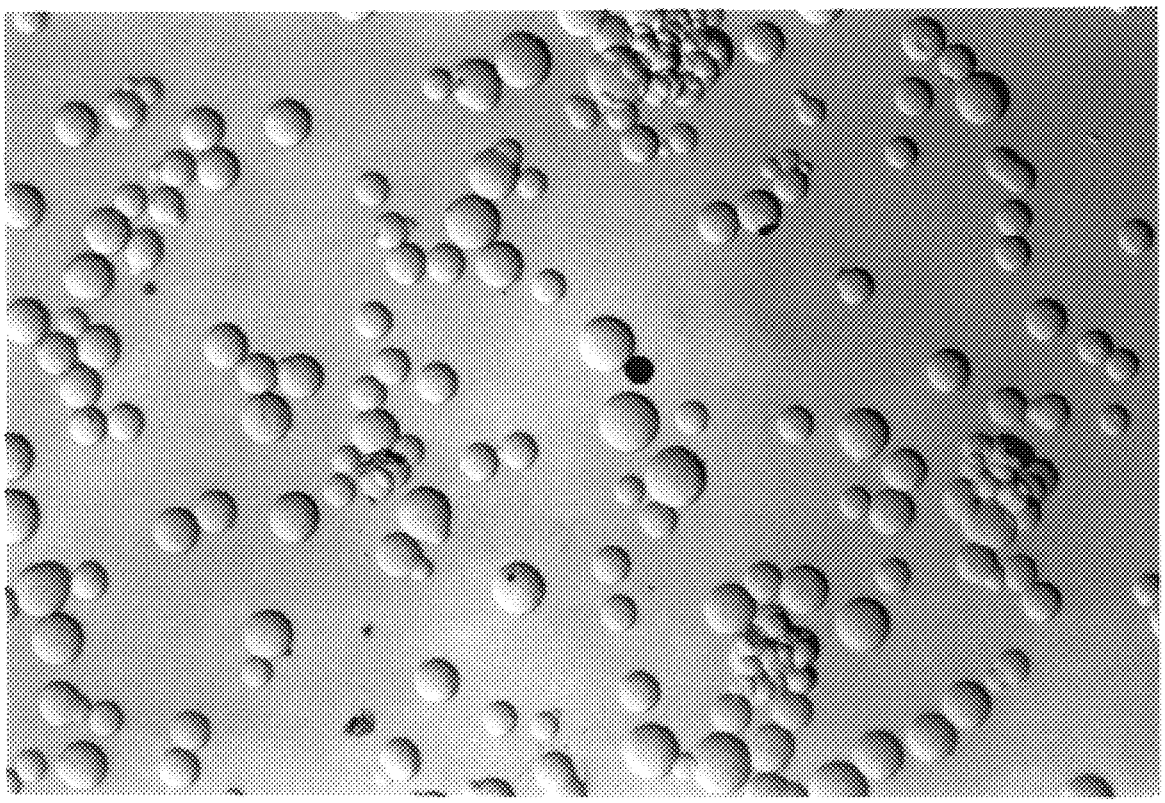

FIG. 6. Photograph of a mixture of "long v-mos" beads and "short v-mos" beads labeled with the anti-v-mos antibody and a secondary antibody.

Figure 7A:
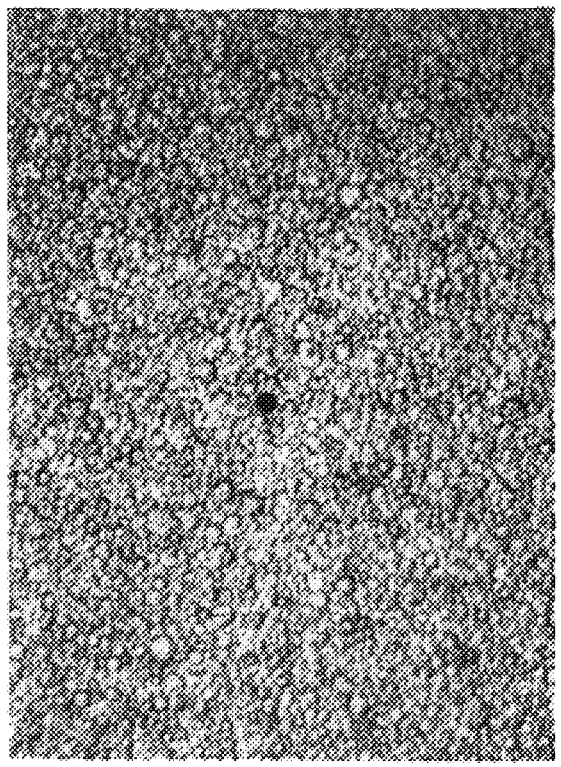
Figure 7B:
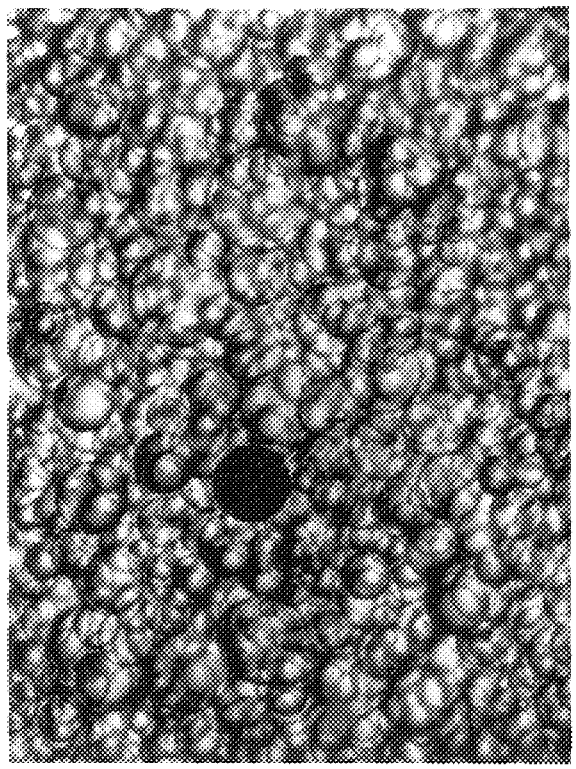
Figure 8A:
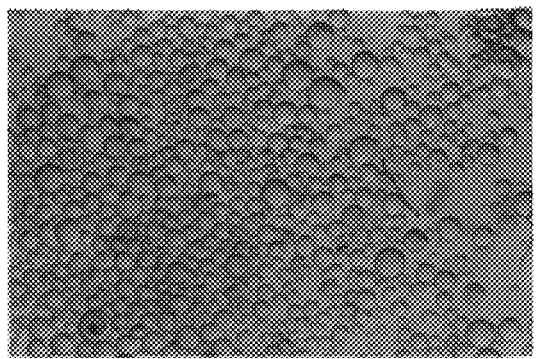
Figure 8B:
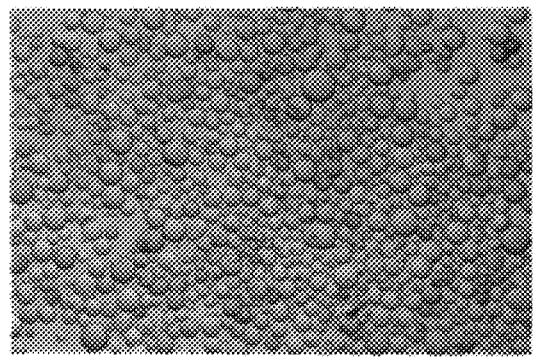
Figure 8C:
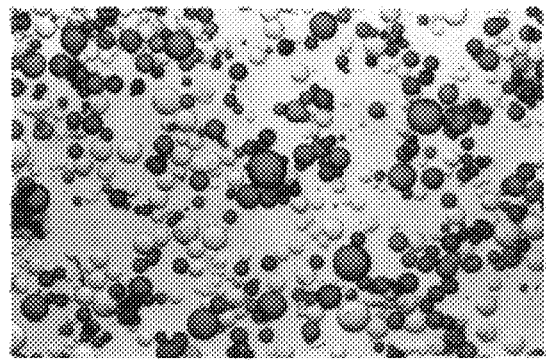
Figure 8D:
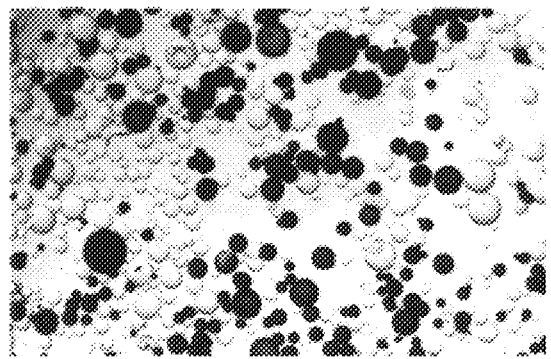

FIG. 7. Photomicrograph of a typical peptide ligand library screening in which a positive (dark blue) bead can easily be identified in a background of many thousands of negative (colorless) beads.

FIG. 8. Photomicrograph showing the concentration-dependent inhibitory effect of biotin on the staining of the LHPQF-resin mimotope beads by streptavidin-alkaline phosphatase. A: 100 nM; B: 10 nM; C: 1 nM; and D: 0.1 nM biotin. Blank beads (β-Ala-aminocaproic acid-resin) were mixed 1:1 with the LHPQFD-resin prior to incubating with streptavidin-alkaline phosphatase to serve as an internal negative control.

5. DETAILED DESCRIPTION OF THE INVENTION

Reference will now be made in detail to the presently preferred embodiments of the invention.

As used herein, the term "library" refers to a collection of substantially random bio-oligomers. As used herein, the term "bio-oligomer" refers to a polymer of less than about 100 subunits. A bio-oligomer of the instant invention may be a peptide, i.e., comprised of amino acid subunits, or an oligonucleotide, i.e., comprised of nucleoside subunits, or a peptide-oligonucleotide chimera.

5.1. METHODS OF GENERATING A RANDOM BIO-OLIGOMER LIBRARY

As stated above, the present invention relates to a method of generating a bio-oligomer library by synthesizing bio-oligomers of random monomer subunit sequences. As used herein, the term "random monomer subunit sequences" refers to sequences in which any monomer subunit may proceed or follow any other monomer subunit.

In one embodiment, the monomer subunit may be an amino acid, an amino acid analog, or a peptidomimetic. As used herein, "peptidomimetic" means a molecule that structurally and chemically resembles a peptide of two or more amino acids. In another embodiment, the monomer subunit may be a nucleoside; the nucleoside may be ribonucleic acid or it may be deoxyribonucleic acid. In yet another embodiment, monomer subunits may be amino acids and nucleosides. The bio-oligomer may be a peptide (comprising amino acids), an RNA oligonucleotide (comprising ribonucleosides), a DNA oligonucleotide (comprising deoxyribonucleosides), a DNA-RNA chimeric oligonucleotide, or a peptide-oligonucleotide chimera. A library comprising peptides, oligonucleotides, or peptide-oligonucleotide chimeras may be generated by a method comprising repeating the step of:

(i) providing at least two aliquots of a solid phase support for the random subunit sequences;

(ii) separately introducing a set of subunits to the aliquots of the solid phase support;

(iii) completely coupling the subunits to substantially all the sites of the solid phase support to form a solid phase support/new subunit combination;

(iv) assessing the completeness of coupling and, if necessary, forcing the reaction to completeness;

(v) thoroughly mixing the aliquots of the solid phase support/new subunit combination;

and, after repeating steps (i)–(v) the desired number of times, a final step of (vi) removing the protecting groups such that bio-oligomer remains linked to the solid phase support. In a further embodiment, the random bio-oligomer library may be prepared such that for at least one step the same subunit is coupled to all of the solid phase supports, and in at least one other step at least two subunits are coupled to the solid phase support. A random bio-oligomer library may be generated by one repetition of steps (i)–(v), above; in another embodiment, the random bio-oligomer library may be generated by more than one repetition of steps (i)–(v) above. A solid phase support may be provided with one or more subunits already coupled.

A bio-oligomer library may be composed of a predetermined, limited number of subunits. In another embodiment, the random bio-oligomer library may be composed of all available subunits.

In a further embodiment, a bio-oligomer of interest may be identified in a sequential process, by first preparing a library and identifying a bio-oligomer sequence that demonstrates properties of interest. A solid phase support comprising the bio-oligomer sequence thus identified is prepared. A new segment of monomer subunit sequences is added to the previously identified sequence, and a new sequence comprising a known sequence and a random sequence that demonstrates properties of interest is identified. This sequential optimization-randomization strategy allows the rapid identification of a bio-oligomer of interest.

The bio-oligomers of the library of the invention may be, but need not be, present in the library in substantially equimolar amounts. As would be familiar to one of ordinary skill in the art, a molar amount is a concentration in which one molecular weight in grams (one mole) of a substance is dissolved in enough solvent to make one liter of solution. As used herein, "substantially equimolar amounts" of bio-oligomers refers to monomer subunit species that are present in approximately the same concentration. Thus, if, in a collection of 150,000 bio-oligomers, bio-oligomer A is present at 200 pmoles/liter, then all the rest of the 150,000 bio-oligomer species will be present at concentrations of approximately 200 pmole/liter. However, as used herein, the term substantially equimolar amount is interpreted to account for heterogeneity of solid phase support sizes. Heterogeneity of solid phase support results in variation in the amount of bio-oligomer that can be attached to a given support.

In the method of the invention, at least two aliquots of solid phase support are provided wherein the number of solid phase supports in the aliquots preferably correspond to at least the number of bio-oligomers to be synthesized. This permits the creation of a library in which each solid phase support contains a single bio-oligomer species, i.e., one bead-one bio-oligomer. As used herein, "aliquot" refers to a part that is a definite fraction of the whole amount of solid phase supports.

5.2. RANDOM PEPTIDE LIBRARIES

In a particular embodiment, the random bio-oligomer library may comprise peptides. The term "peptide" is used in its broadest sense to refer to a compound of two or more subunit amino acids, amino acid analogs or peptidomimetics. The subunits may be linked by peptide bonds. In another embodiment, the subunit may be linked by other the bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The present invention is based on synthetic peptide chemistry and does not rely on any living system for amplification or screening. Peptide libraries can include unnatural amino acids. Thus, peptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties to peptides in the library.

Additionally, by assigning specific amino acids at specific coupling steps, peptide libraries with α-helices, β turns, β sheets, γ-turns, and cyclic peptides can be generated.

The library of peptides of the invention includes all possible combination of amino acids of which the peptides are composed. Using as an example a dipeptide made up of the two amino acids glycine and proline, there are four possible combinations: glycine-glycine, glycine-proline, proline-glycine, and proline-proline, and the random library will contain all four combinations.

A set of first amino acids is separately introduced to each aliquot. Generally, the amino acids used for peptide synthesis are the base-labile $N^\alpha$-amino protected 9-fluorenylmethoxycarbonyl (Fmoc) amino acids first described by Carpino and Han (1972, J. Org. Chem. 37:3403–3409). The method of the present invention may also be used with the Boc-amino acids ($N^\alpha$-amino protected $N^\alpha$-t-butyloxycarbonyl). Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art.

Continuing with the dipeptide example described above, the first set of amino acids introduced would comprise glycine and proline; each aliquot receives either an $N^\alpha$-Fmoc-glycine or an $N^\alpha$-Fmoc-proline.

After introduction, the set of first amino acids is completely coupled to substantially all the sites of the solid phase supports. As used herein, complete coupling means that the coupling reaction is driven to completion irrespective of the differences in the coupling rates of individual amino acids. In addition, the amino acids are coupled to substantially all available coupling sites on the solid phase support so that each solid phase support will contain essentially only one species of peptide. Complete coupling will result in solid phase support/first amino acid combinations. Using the dipeptide described above as an example, the completion of the coupling will yield a bead-glycine combination and a bead-proline combination.

The coupling of the amino acids may be accomplished by techniques familiar to those in the art and provided, for example, in Stewart and Young, 1984, Solid Phase Synthesis, Second Edition, Pierce Chemical Co., Rockford, Ill. As would be known to those of ordinary skill in the art, the process of peptide synthesis on solid supports generally involves building a peptide from the carboxyl or C-terminal end in which the C-terminal amino acid with its α-amino group protected is attached to a solid phase polymer. The protecting group is then cleaved off, and the next amino acid, also protected, is coupled by a peptide bond to the a-amino group of the amino acid attached to the solid support. The cycle of deprotection of the prior amino acid and coupling the additional amino acid is repeated until the peptide is completed. Any reactive side chains of the amino acids are protected by chemical groups that can withstand the coupling and $N^\alpha$-deprotection procedure but can be removed at the end of the synthesis.

In order to couple an amino acid to the growing synthetic chain, the carboxyl group of the blocked amino acid must be activated. Many methods of activation may be used in the practice of the invention and include, for example, preformed symmetrical anhydrides (PSA), preformed mixed anhydride (PMA), acid chlorides, active esters, and in situ activation of the carboxylic acid, as set forth in Fields and Noble, 1990, "Solid phase peptide synthesis utilizing 9-fluorenylmethoxycarbonyl amino acids", Int. J. Pept. Protein Res. 35:161–214.

The use of Fmoc amino acids is but one strategy of peptide synthesis. A Boc (t-butyloxycarbonyl-protected amino group) strategy may also be used to prepare a library of peptides bound to the solid phase support (e.g., Geysen et al., 1987,. J. Immunol. Methods 102:259–274.)

The completeness of coupling should be assessed. Those skilled in the art would be familiar with the well known quantitative monitoring tests such as ninhydrin (the Kaiser test), picric acid, 2,4,6-trinitrobenzenesulfonic (TNBS), fluorescamine, and chloranil, which are based on reagent reaction with free amino groups to produce a chromophoric compound. If imino acids (e.g., Pro and Hyp) are used, isatin monitoring is a preferred method. Fields and Noble, supra. Quantification of reaction completeness may be monitored during the course of the reaction, e.g., as described by Salisbury et al. (International Patent Publication No. WO91/03485).

With Fmoc synthesis, the Kaiser test is preferred. In the Kaiser test, a sample from each tube can be tested with ninhydrin reagent obtained from Pierce Chemical in the method set forth by Sarin et al. (1981, Anal. Biochem. 117:147–157.)

If the coupling reaction is incomplete as determined by this test, the reaction can be forced to completion by several methods familiar to those in the art, including (a) a second coupling using a one to five fold excess of protected amino acid, (b) an additional coupling using different or additional solvents (e.g., trifluoroethane), or (c) the addition of chaotropic salts, e.g., $NaClO_4$ or LiBr (Klis and Stewart, 1990, "Peptides: Chemistry, Structure and Biology," Rivier and Marshall, eds., ESCOM Publ., p. 904–906).

After the coupling reaction is complete the aliquots of the solid phase support/first amino acid combinations are thoroughly mixed. Thorough mixing is obtained when a uniform mixture of the aliquots results, preferably by mixing the aliquots in a single reaction vessel. Although any means of thorough mixing is within the scope of this invention and a variety of means are familiar to those of ordinary skill in the art, preferable means may include, for example, vortexing or shaking in any commercially available motorized shaker apparatus or by bubbing with inert gas, e.g., nitrogen or argon.

The resulting mixture is divided into at least two aliquot parts. These aliquot parts are equal in volume and, if the mixing was sufficiently thorough, should contain substantially equal amounts of the solid phase support/first amino acid combinations. Using the dipeptide example, each aliquot will contain essentially equal amounts of the bead-glycine combination and the bead-proline combination.

To each aliquot is separately introduced a second set of amino acids. This second set may consist of (a) the same amino acids added in the first set, i.e., glycine or proline; (b) a different set of amino acids, e.g., tryptophan or leucine; (c) only one type of amino acid, e.g., isoleucine.

As with the first set of amino acids, the second set of amino acids is completely coupled individually to the solid phase support/first amino acid combination of each aliquot to form peptides comprising a first amino acid and a second amino acid. As with the prior coupling, the coupling may be accomplished by any technique used in the art for such reactions. Using the dipeptide example discussed above: (a) with the addition of the same set of amino acids, the resulting peptides are either glycine-glycine, glycine-proline, proline-glycine, or proline-proline (b) with a different set of amino acids, the resulting peptides are either Gly-Trp, Gly-Leu, Pro-Trp or Pro-Leu; (c) with one type of amino acid, the resulting peptides are Gly-Ile or Pro-Ile.

This method can be repeated as many times as there are amino acids to add. If the peptide of interest is a tetrapeptide X-X-X-Trp, where X is either valine, serine or alanine, for example, the method can be repeated three times to get the X-X-X-Trp tetrapeptide. In the first, second, and third introductions of amino acids, either a $N^\alpha$-Fmoc valine, $N^\alpha$-Fmoc serine($O$-$Bu^t$), or $N^\alpha$-Fmoc alanine is added to the aliquots of solid phase support to yield 27 different peptides of substantially equimolar amounts (FIG. 1). If a hexapeptide is desired, the process is repeated six times. If the hexapeptide is to be comprised of five different amino acids, the method could be employed using five aliquots, each containing a different amino acid, at each coupling step. If, however, the hexapeptide is to be comprised of any of the basic set of twenty amino acids, the method could be employed using twenty aliquots at each coupling step.

The method of the peptide synthesis of the invention can be used with solid phase supports to which an amino acid either is or is not already attached. In addition, one may use a linker that has already been attached to the solid phase support. One common support to which an amino acid is already bound is the β-alanine-PAM-resin (obtained from Bachem Biochemical). These resins are available from numerous commercial sources or made in the laboratory by one knowledgeable in the art of peptide synthesis.

If a solid phase support/amino acid combination or solid phase/support linker is used as the initial reagent, it is divided into at least two aliquots, each of which receives an amino acid from a first set of amino aids. As described above, the first set of amino acids is completely coupled to substantially all binding sites on the solid phase support/amino acid combination or solid phase support/linker and the aliquots containing these newly added amino acids are thoroughly mixed. As described above, the mixture is divided into at least two aliquots, each aliquot receives an amino acid from a second set of amino acids, and the coupling reaction is repeated to form a growing peptide. As described above, the process can be repeated as many times as is desired to produce the peptides of interest.

This method may be used for the synthesis of random peptides as well as for the synthesis of a peptide library that comprises pre-determined sequences. The synthesis of pre-determined sequences involves the use of specific $N^\alpha$-Boc-, $N^\alpha$-Fmoc- or other appropriately protected amino acids during specific coupling steps. For example, one may select amino acids at specific coupling steps such that the resulting peptides will have a probability or preference for a particular secondary structure, e.g. β-sheet, α-helix, β-turn, etc. For example, α-helix would be preferred if Glu, Ala, Leu, His, Trp are used as preferred amino acids; on the other hand β-sheets would be preferred if Val, Ile, Tyr and Met are used. Alternatively, if Gly, Asn, Ser, Pro, Asp are used, a β-turn structure would be preferred. Other examples could be considered such as acidic amino acids near the N-terminal, and basic amino acids near the C-terminal, to stabilize an α-helix. D-amino acids can stabilize certain turns, and numerous other structural motifs can be incorporated (See Sections 5.2.1. and 5.2.2., infra). It may even be possible to prepare cyclic peptide libraries with disulfide, lactam, lactone or other ring closing moieties (See Section 5.2.1., infra).

It is to be emphasized that the method of the instant invention allows the synthesis of peptides such that each solid phase support, such as a resin bead, will contain only one species of peptide. The method assures that each individual resin bead is in contact with only one Fmoc amino acid during each coupling cycle and that the coupling is driven to completion. The one bead-one peptide synthesis allows increased sensitivity and efficiency of isolating the peptide that is specific for the entity to which is binds.

The method may be readily applied to permit the synthesis of a random peptide pool with $10^5$ to $10^7$ different peptide species.

In one aspect of the invention, the peptides of a library may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bond to the bead. In one embodiment, the pseudo-free C-terminal residue may be of the D or the L optical configuration; in another embodiment, a racemic mixture of D and L-isomers may be used.

In an additional embodiment, pyroglutamate may be included as the N-terminal residue of the peptides of the library. Although pyroglutamate is not amenable to sequence by Edman degradation, by limiting substitution to only 50% of the peptides on a given bead with N-terminal pyroglutamate, there will remain enough non-pyroglutamate peptide on the bead for sequencing. One of ordinary skill would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

In a further embodiment, subunits of peptides that confer useful chemical and structural properties will be chosen. For example, peptides comprising D-amino acids will be resistant to L-amino acid-specific proteases in vivo. In addition, the present invention envisions preparing libraries of peptides that have more well defined structural properties, and the use of peptidomimetics, and peptidomimetic bonds, such as ester bonds, to prepare libraries with novel properties. In another embodiment, a peptide library may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such libraries would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et al., 1990, Biochem J. 268:249–262); the present invention provides a method to produce a constrained peptide that incorporates random sequences at all other positions.

5.2.1. CONSTRAINED AND CYCLIC PEPTIDES

A constrained, cyclic or rigidized peptide may be prepared according to the method described supra, provided that in at least two positions in the sequence of all peptides of the library an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94:1128–1132). A peptide library in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The instant invention provides a set of general rigid motifs for use in preparing libraries according to the present invention. In one embodiment, shown in FIG. 2a, two pair of crosslinking residues are arranged to create a "basket". Such a "basket" motif may have particular application as a catalytic pocket, in addition to novel binding properties resulting from its constrained conformation. In another embodiment comprising two pair of crosslinking residues, a "ladder" motif, shown in FIG. 2b, may be engineered. By the alternating use of D-and L-amino acids in a "ladder" motif, a peptide in which all of the side chains would orient at one surface, analogous to the β-barrel found in gramicidin, may be prepared. Such a surface may potentially provide a unique catalytic site. In yet a further embodiment, a simple "lariat" motif may be created, in which two residues form a cross-link, as shown in FIG. 2c. In addition to providing a peptide loop, a shorter "lariet" motif would result in a conformationally constrained linear peptide, thus stabilizing secondary structure, e.g., an alpha helix.

It is further envisioned that interpeptide crosslinks may be formed resulting in a rigid peptide matrix.

The present invention provides strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137–167; Ponsanti et al., 1990, Tetrahedron 46:8255–8266). The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

5.2.2. NON-CLASSICAL AMINO ACIDS THAT INDUCE CONFORMATIONAL CONSTRAINTS

The following non-classical amino acids may be incorporated in the random peptide library in order to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3R)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a selectide library to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); α-helix inducing analogs (Kemp et al., 1988, Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436.

Although the foregoing non-classical peptides and peptidomimetics may not be amenable to classical Edman degradation sequence analysis, a combination of initial Edman degradation followed by amino acid analysis of the residual chain can be used to determine the structure of a peptide with desired activity. Alternatively, mass spectral analysis may be employed.

5.2.3. DERIVATIZED AND MODIFIED PEPTIDES

The present invention further provides for modification or derivatization of peptides in a library. Modifications of peptides are well known to one of ordinary skill, and include phosphorylation, carboxymethylation, and acylation. Modifications may be effected by chemical or enzymatic means.

In another aspect, glycosylated or fatty acylated peptide derivatives may be prepared. Preparation of glycosylated or fatty acylated peptides is well known in the art as exemplified by the following references;

1. Garg and Jeanloz, 1985, in Advances in Carbohydrate Chemistry and Biochemistry, Vol. 43, Academic Press.
2. Kunz, 1987, in Ang. Chem. Int. Ed. English 26:294–308.
3. Horvat et al., 1988, Int. J. Pept. Protein Res. 31:499–507.
4. Bardaji et al., 1990, Ang. Chem. Int. Ed. English, 23:231.
5. Toth et al., 1990, in Peptides: Chemistry, Structure and Biology, Rivier and Marshal, eds., ESCOM Publ., Leiden, pp. 1078–1079.
6. Torres et al., 1989, Experientia 45:574–576.
7. Torres et al., 1989, EMBO J. 8:2925–2932.
8. Hordever and Musiol, 1990, in Peptides: Chemistry, Structure and Biology, loc. cit., pp. 811–812.
9. Zee-Cheng and Olson, 1989, Biochem. Biophys. Res. Commun. 94:1128–1132.
10. Marki et al., 1977, Helv. Chem. Acta., 60:807.
11. Fuju et al. 1987, J. Chem. Soc. Chem. Commun., pp. 163–164.

12. Ponsati et al., 1990, Peptides 1990, Giralt and Andreu, eds., ESCOM Publ., pp. 238–240.
13. Fuji et al., 1987, 1988, Peptides: Chemistry and Biology, Marshall, ed., ESCOM Publ., Leiden, pp. 217–219.

There are two major classes of peptide-carbohydrate linkages. First, ether bonds join the serine or threonine hydroxyl to a hydroxyl of the sugar. Second, amide bonds join qlutamate or asparatate carboxyl groups to an amino group on the sugar. In particular, references 1 and 2, supra, teach methods of preparing peptide-carbohydrate ethers and amides. Acetal and ketal bonds may also bind carbohydrate to peptide.

Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure—$(CH_2)_aCH_3$ may be incorporated in peptides of the library. This and other peptide-fatty acid conjugates suitable for use in the present invention are disclosed in U.K. Patent GB-8809162.4, International Patent Application PCT/AU89/00166, and reference 5, supra.

5.3. RANDOM OLIGONUCLEOTIDE LIBRARIES

The method for the synthesis of a selectide library composed of nucleic acids can be adapted from the solid phase synthesis of DNA by phosphoramidate method pioneered by Caruthers (1985, Science 230:281; Caruthers et al., 1987, Methods in Enzymology 154:287–313).

Both silica-based insoluble polymeric support as well as protected deoxynucleosides are commercially available (e.g., Peninsula Laboratories, Inc., California, Applied Biosystems, Inc.). Examples of the protected deoxynucleosides are 5'-0-dimethoxytrityldeoxythymidine, 5'-0-dimethoxytrityl-4-N-benzoyldeoxycytidine, 5'0-dimethoxytrityl-N-benzoyldeoxyadenosine, and 5'-0-dimethoxytrityl-N-isobutyldeoxyguanosine. Other specific protecting groups can be used depending on the application. The corresponding deoxynucleoside 3'-phosphoramidites can be synthesized and subsequently coupled to the solid support according to Caruthers et al., 1987, supra. The first deoxynucleoside could be fixed, for example, as deoxyadenosine. After detritylation, and washing with dichloromethane followed by acetonitrile, the solid-support is separated into four equal aliquots and transferred into four separate reaction vessels. The four deoxynucleoside 3'-phosphoramidites are then added individually into the four separate reaction vessels. After the completion of coupling the solid-supports from the four reaction vessels are mixed together, thoroughly washed and then subjected to oxidation with a mixture of $I_2/H_2O$/lutidine/THF. After oxidation, the solid-support is thoroughly washed with acetonitrile and the above cycle repeated. After the random polydeoxynucleotide chain synthesis has been completed (e.g., after 11 coupling steps), the methyl ester groups will be cleaved by thiophenol, and the DMT group will be cleaved by trichloracetic acid. The deprotected polynucleotide chains can remain covalently attached to the solid support (when appropriate linkers are chosen), ready to be used in the selected screening methodology as outlined infra.

The present invention provides that oligonucleotides with other than phosphodiester bonds may be used. For example, an oligonucleotide may incorporate a phosphorothionate linkage. Other modified phosphodiester bonds or bond analogs are well known in the art. Such modified linkages are known to be resistant to exonuclease and endonuclease activity.

Since there are only four DNA or RNA nucleosides per coupling step, in a library with 12 nucleoside bases, there will be $4^{12}$ possible polynucleotide sequences, i.e., a total of $1.68 \times 10^7$ possibilities. Moreover, an oligonucleotide may be synthesized using both DNA and RNA nucleosides. One of ordinary skill would also recognize that in addition to the major nucleosides, uncommon and modified nucleosides may also be used. Uncommon and modified nucleosides include inosine, methylated purine nucleosides, uridine derivatives, and 2'-0-methylribose, which can occur with any ribonucleoside.

5.4. SOLID PHASE SUPPORTS AND LINKERS FOR USE IN A RANDOM BIO-OLIGOMER LIBRARY

A solid phase support for use in the present invention will be inert to the reaction conditions for bio-oligomer synthesis, e.g., peptide synthesis or oligonucleotide synthesis, or both. A solid phase support for use in the present invention must have reactive groups in order to attach a monomer subunit, or for attaching a linker or handle which can serve as the initial binding point for a monomer subunit. In one embodiment, the solid phase support may be suitable for in vivo use, i.e., it may serve as a carrier for or support for direct applications of the bio-oligomer library (e.g., TentaGel, Rapp Polymere, Tubingen, Germany; see Section 5.8., infra). In a particular embodiment, the solid phase support may be palatable and orally consumable. In another embodiment, the solid phase support may be a useful chromatographic support.

As used herein, solid phase support is not limited to a specific type of support. Rather a large number of supports are available and are known to one of ordinary skill in the art. Solid phase supports include silica gels, resins, derivatized plastic films, glass beads, cotton, plastic beads, alumina gels. A suitable solid phase support may be selected on the basis of desired end use and suitability for various synthetic protocols. For example, for peptide synthesis, solid phase support may refer to resins such as polystyrene (e.g., PAM-resin obtained from Bachem Inc., Peninsula Laboratories, etc.), POLYHIPEO resin (obtained from Aminotech, Canada), polyamide resin (obtained from Peninsula Laboratories), polystyrene resin grafted with polyethylene glycol (TentaGels, Rapp Polymere, Tubingen, Germany) or polydimethylacrylamide resin (obtained from Milligen/Biosearch, California). In a preferred embodiment for peptide synthesis, solid phase support refers to polydimethylacrylamide resin.

The solid phase supports of the invention may also comprise a linker. As used herein, a linker refers to any molecule that provides spatial distance between the support and the peptide to be synthesized. Linkers can be covalently attached on the solid phase support prior to coupling with a $N^\alpha$-Boc or $N^\alpha$-Fmoc or otherwise appropriately protected amino acids. Various linkers can be used to attach the oligomer to solid phase support. Examples of linkers include aminobutyric acid, aminocaproic acid, 7-aminoheptanoic acid, and 8-aminocaprylic acid. Fmoc-aminocaproic acid is commercially available from Bachem Biochem, and is the preferred embodiment. In a further embodiment, linkers can additionally comprise one or more β-alanines as spacers. In addition, the solid-support could be modified to meet specific requirements for the particular purpose of bioassay or detection. Modification of solid phase support may be made by incorporation of a specific linker. For example, modified solid-phase support could be made acid-sensitive, base-sensitive, nucleophilic-sensitive, electrophilic sensitive, photosensitive, oxidation sensitive or reduction sensitive.

In addition to the linkers described above, selectively cleavable linkers may be employed. Use of an ultraviolet light sensitive linker, ONb, is shown in Section 12, infra (see Barany and Albenicia, 1985, J. Am. Chem. Soc. 107:4936–4942). Other cleavable linkers require hydrogenolysis or photolysis. Examples of photosensitive (photocleavable) linkers are found in Wang (1976, J. Org. Chem. 41:32–58), Hammer et al. (1990, Int. J. Pept. Protein Res. 36:31–45), and Kreib-Cordonier et al. (1990, in Peptides—Chemistry, Structure and Biology, Rivier and Marshall, eds., pp. 895–897). Landen (1977, Methods Enzym. 47:145–149) used aqueous formic acid to cleave Asp-Pro bonds; this approach has been used to characterize T-cell determinants in conjunction with the Geysen pin synthesis method (Van der Zee et al., 1989, Eur. J. Immunol. 191:43–47). Other potential linker groups cleavable under basic conditions include those based on p-(hydroxylmethyl) benzoic acid (Atherton et al., 1981, J. Chem. Soc. Perkin I:538–546) and hydroxyacetic acid (Baleaux et al., 1986, Int. J. Pept. Protein Res. 28:22–28). Geysen et al. (1990, J. Immunol. Methods 134:23–33) reported peptide cleavage by a diketopiperazine mechanism. An enzyme may specifically cleave a linker that comprises a sequence that is sensitive or a substrate for enzyme cleavage, e.g., protease cleavage of a peptide; endonuclease cleavage of an oligonucleotide. In certain instances, one may derivatize 10–50% of the resin by substitution with the cleavable linker, and the remaining 50–90% substituted with a noncleavable linker to ensure that enough peptide will remain after cleavage of linker be left behind for sequencing. Combinations of cleavable linkers can also be used to allow sequential cleaving from a single bead.

A solid phase support for use in the present invention may further comprise a bio-oligomer of interest, to which a random subunit sequence may be added. The pre-attached bio-oligomer may be selected according to the methods described herein, or may comprise a sequence known to embody desired properties.

In synthesis of oligonucleotides, a silica based solid phase support may be preferred. As discussed in Section 5.3., supra, silica based solid phase supports are commercially available (e.g., from Peninsula Laboratories, Inc.; and Applied Biosystems, Inc.).

5.5. METHODS OF DETECTION AND IDENTIFICATION OF BIO-OLIGOMERS OF INTEREST

In addition to providing truly random libraries of bio-oligomers, and methods of synthesis thereof, the present invention further comprises methods of screening a bio-oligomer library to identify bio-oligomers within the library that demonstrate a biological activity of interest, such as binding, stimulation, inhibition, toxicity, taste, etc. Other bio-oligomer libraries may be screened according to the methods described infra for enzyme activity, enzyme inhibitory activity, and chemical and physical properties of interest.

The bio-oligomers of interest discovered during an initial screening need not be the final ligands. In fact, it is preferable to synthesize a second library based on the common sequences of the ligands selected during the first screening. In this way, one may be able to identify ligands of even higher activity provided that the second screening is done under conditions of much higher stringency.

5.5.1. BINDING ASSAYS

The present invention allows identification of bio-oligomer ligands that bind acceptor molecules. As used herein, the term "acceptor molecule" refers to any substance which binds to a bio-oligomer ligand. Acceptor molecules may be a biologic macromolecule such as, but not limited to, antibodies, receptors, or viruses. In addition, acceptor molecules may be a chemical compound such as, but not limited to, proteins, carbohydrates, nucleic acids, lipids, drugs, metals or small molecules.

The bio-oligomer library of the invention can potentially interact with many different acceptor molecules. By identifying the particular bio-oligomer species to which a specific acceptor molecule binds, it is possible to physically isolate the bio-oligomer species of interest.

Because only a small number of beads will be removed during each screening/detection/isolation step, the majority of the beads will remain in the pool. Therefore, the random bio-oligomer library can be reused multiple times. If different color or identification schemes are used for different acceptor molecules (e.g., with fluorescent reporting groups such as fluorescein (green), Texas Red (Red) and DAPI (blue) tagged on the acceptors), and with suitable excitation filters in the fluorescence microscope or the fluorescence detector, different acceptors (receptors) can be added to a peptide library and evaluated simultaneously to facilitate rapid screening for specific ligands. These strategies not only reduce cost, but also increase the number of acceptor molecules that can be screened.

In the method of the invention, an acceptor molecule of interest is introduced to the library of bio-oligomers where it will recognize and bind to one or more bio-oligomer species within the library. Each bio-oligomer species to which the acceptor molecule binds will be found on a single solid phase support so that the support, and thus the bio-oligomer, can be readily identified and isolated.

The bio-oligomer can be isolated by any conventional means known to those of ordinary skill in the art and the invention is not limited by the method of isolation. For example and not by way of limitation, it is possible to physically isolate a solid phase support/bio-oligomer combination that exhibits the strongest physico-chemical interaction with the specific acceptor molecule. In one embodiment based on physico-chemical interaction, a solution of a specific acceptor molecule added to a random peptide library which is equivalent to approximately $10^5$ to $10^7$ solid phase supports. The acceptor molecule is incubated with the resin for a time sufficient to allow coupling between the peptide and antibody, for example, one hour at 22° C. Thereafter, the acceptor molecule coated bio-oligomer/solid phase support is isolated. More specific embodiments are set forth in the following methods, which describe the use of a monoclonal antibody as a soluble acceptor molecule. It will be clear that these methods are readily adaptable to detect binding of any acceptor molecule. Furthermore, although the following refers to libraries of peptides, it will be understood that libraries of oligonucleotides or peptide-oligonucleotide chimeras may also be assayed.

(i) The monoclonal antibody is first labeled with a fluorescent moiety or "fluoresceinated" by techniques that are within the routine skill of those in this art. The antibody at a concentration of 1 ug/ml is then introduced to the library of peptides and, after gentle mixing at 22° C. for one hour, the solid phase supports are washed, and the fluorescent antibody solid phase support/peptide combinations are identified and recovered with a fluorescence activated cell sorter. Alternatively, the fluorescent antibody solid phase support/peptide combinations are identified and physically picked up under a dissecting microscope with fluorescent attachment using a micromanipulator. The relative intensity of fluorescence is generally proportional to the affinity of the peptide-ligand to the monoclonal antibody in question.

(ii) The monoclonal antibody is first conjugated onto ferro-magnetic beads by techniques that are routine in the art. The conjugated antibody at a concentration of 1 ug/ml is then incubated with the library for one hour at 22° C. The magnetic beads will form a rosette around the solid phase support/peptide of interest which can then be physically isolated with a strong magnet.

(iii) The monoclonal antibody is first conjugated to an enzyme such as alkaline phosphatase by techniques that are routine in the art. This antibody-enzyme conjugate is then incubated with the random peptide library for 30 minutes to one hour at 22° C. After washing, the whole library is poured into a petri dish which contains a substrate for alkaline phosphatase, for example, 5-bromo-4-chloro-3-indoyl phosphate (BCIP) and nitro-blue tetrazoleum (NBT). After incubating for several minutes, the antibody-solid phase support/peptide combination changes color (becomes blue) due to precipitation of the converted substrate on the solid phase support, and can be easily identified and isolated physically under a dissecting microscope with a micromanipulator. The relative intensity of the color reaction is generally proportional to the affinity of the peptide for the monoclonal antibody in question.

(iv) The monoclonal antibody is first conjugated to an enzyme such as horseradish peroxidase by techniques that are routine in the art. This antibody-enzyme conjugate is then incubated with the random peptide library for 30 minutes to one hour at 22° C. After washing, the whole library is poured into a petri dish which contains a substrate for peroxidase, for example, 3,3',4,4'-diaminobenzidine (DAB); 3,3',5,5'-tetramethylbenzidine (TMB); or 4-chloro-1-napthol (4CN). After incubating for several minutes, the antibody-solid phase support/peptide combination changes color, and can be identified and isolated physically under a dissecting microscope with a micromanipulator. The relative intensity of the color reaction is generally proportional to the affinity of the peptide for the monoclonal antibody in question.

(v) The monoclonal antibody is first labeled with biotin or "biotinylated" by techniques that are routine in the art and is thereafter incubated with the random peptide library for 30 minutes to one hour at 22° C. After washing, a streptavidin-alkaline phosphatase or streptavidin-horseradish peroxidase complex is added and incubated for 30 minutes. The support is then washed, and the color is developed as described above in (iii) with the enzyme method. The peptide/solid phase support of interest is physically isolated as above.

In addition to using soluble acceptor molecules, in another embodiment, it is possible to detect bio-oligomers that bind to cell surface receptors using intact cells. The use of intact cells is preferred for use with receptors that are multi-subunits or labile or with receptors that require the lipid domain of the cell membrane to be functional. The cells used in this technique may be either live or fixed cells. The cells will be incubated with the random peptide library and will bind to certain peptides in the library to form a "rosette" between the target cells and the relevant solid phase support/peptide. The rosette can thereafter be isolated by differential centrifugation or removed physically under a dissecting microscope.

Alternatively, one may screen the library using a panning procedure with cell lines such as (i) a "parental" cell line where the receptor of interest is absent on its cell surface, and (ii) a receptor-positive cell line, e.g., a cell line which is derived by transfecting the parental line with the gene coding for the receptor of interest. It is then possible to screen the library by the following strategy: (i) first depleting the library of its non-specific beads that will bind to the cells lacking the receptor by introducing a monolayer of parental cell line by the standard "panning technique" to leave receptor-specific non-binding beads, or irrelevant non-binding beads (ii) removing the non-binding beads which will include both receptor-specific or irrelevant beads and loading them on a monolayer of receptor positive cell line in which the receptor-specific bead will bind to the receptor positive cell line, (iii) removing the remaining irrelevant non-binding beads by gentle washing and decanting, and (iv) removing the receptor-specific bead(s) with a micromanipulator.

As an alternative to whole cell assays for membrane bound receptors or receptors that require the lipid domain of the cell membrane to be functional, the receptor molecules can be reconstituted into liposomes where reporting group or enzyme can be attached.

Although the foregoing examples refer to peptide ligands, any of the bio-oligomers described in Sections 5.1., 5.2. and 5.3., supra, may be used in the practice of the instant invention. Thus, acceptor molecule may bind to non-classical, circularized, conformationally influenced, or structurally constrained peptides, to oligonucleotides, or to peptide-oligonucleotide chimeras.

In one embodiment, the acceptor molecule may be directly labeled. In another embodiment, a labeled secondary reagent may be used to detect binding of an acceptor molecule to a solid phase support containing a bio-oligomer of interest. Binding may be detected by in situ formation of a chromophore by an enzyme label. Suitable enzymes include, but are not limited to, alkaline phosphatase and horseradish peroxidase. In a further embodiment, a two color assay, using two chromogenic substrates with two enzyme labels on different acceptor molecules of interest, may be used. Cross-reactive and singly-reactive ligands may be identified with a two-color assay.

Other labels for use in the invention include colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels. Two color assays may be performed with two or more colored latex beads, or fluorophores that emit at different wavelengths. Labeled beads may be isolated manually or by mechanical means. Mechanical means include fluorescence activated sorting, i.e., analogous to FACS, and micromanipulator removal means.

In specific examples, infra, enzyme-chromogen labels and fluorescent (FITC) labels are used.

Reactive beads may be isolated on the basis of intensity of label, e.g., color intensity, fluorescence intensity, magnetic strength, or radioactivity, to mention a few criteria. The most intensely labeled beads may be selected and sequenced or otherwise characterized as to structure, e.g., by mass spectral analysis. In another embodiment, a random selection of beads with a label intensity above an arbitrary cut-off may be selected and sequenced. One can potentially use modern image analysis microscopy to quantitate the color intensity, and hence precisely define the relative affinity of the ligand to the acceptor molecule prior to the sequence analysis of the bead. Similarly, quantitative immunofluorescence microscopy can be applied if the acceptor is tagged with a fluorescent label. In yet another embodiment, beads demonstrating a certain label intensity are selected for composition analysis, e.g., amino acid composition determination. A refinement library comprising a restricted set of monomer subunits identified as important from the composition analysis may be prepared and screened.

In another embodiment, the bio-oligomer(s) with the greatest binding affinity, i.e., binding constant, may be identified by progressively diluting the acceptor molecule of interest until binding to only a few solid phase supports of the library is detected. Alternatively, stringency of the binding solution, or, in the case of nucleic acids, hybridization with a target nucleic acid, i.e., acceptor molecule, may be increased. One of ordinary skill would understand that stringency of binding or hybridization may be increased by (i) increasing solution ionic strength; (ii) increasing the concentration of denaturing compounds such as urea; (iii) increasing or decreasing pH relative to neutral (pH 7); (iv) in the case of nucleic acids, approaching the $T_m$ (melting temperature). Other means of changing solution conditions to limit binding to high affinity interactions are well known in the art. High dilution or high stringency binding of an acceptor molecule to a solid phase support/bio-oligomer may be used to detect a ligand of interest in a random library comprising all or almost all possible monomer subunits, or in a limited refinement library.

In another embodiment, bio-oligomers that demonstrate low affinity binding may be of interest. These may be selected by first removing all high affinity-binding bio-oligomers and then detecting binding under low stringency or less dilute conditions.

In a preferred embodiment, a dual label assay may be used. The first label may be used to detect non-specific binding of an acceptor molecule of interest to beads in the presence of soluble ligand. Labelled beads are then removed from the library, and the soluble ligand is removed. Then specific binding acceptor molecule to the remaining beads is detected. Bio-oligomers on such beads may be expected to bind the acceptor molecule at the same binding site as ligand of interest, and thus to mimic the ligand of interest. The dual label assay provides the advantage that the acceptor molecule of interest need not be purified since the first step of the assay allows removal of non-specific positive reacting beads.

5.5.2. BIOACTIVITY ASSAYS

The instant invention further provides assays for biological activity of a bio-oligomer from a library treated so as to remove any toxic molecules remaining from synthesis, e.g., by neturalization and exensive washing with solvent, sterile water and culture medium. The biological activities that may be assayed include toxicity and killing, stimulation and growth promotion, and physiological change.

In a preferred embodiment, the bio-oligomers of the library are selectively cleavable from the solid-phase support, also referred to herein as "bead". In one embodiment, beads are prepared such that only a fraction of bio-oligomers are selectively cleavable. Selectively cleavable bio-oligomers, linkers and beads are discussed in Section 5.4., supra. A library is treated with a cleaving agent such that cleavage of a fraction of bio-oligomers occurs. Examples of cleaving agents include, but are not limited to, UV light, acid, base, enzyme, or catalyst. In one embodiment, the library is treated so that 10–90% of the bio-oligomers are released. In a more preferred embodiment, 25–50% of the bio-oligomers are released. Where all bio-oligomers are cleavable, non-quantitative cleavage can be effected by limiting the cleaving agent. In one aspect, exposure time and intensity of UV light is limited. In another embodiment, the concentration of reagent is limited. After treatment to effect cleavage, the library may be further treated, e.g., by neutralization, to make it biologically compatible with the desired assay. In practice, one of ordinary skill would be able to readily determine appropriate cleavage conditions for partial cleavage when all bio-oligomers of the library are attached to solid phase by cleavable linkers or bonds. One of ordinary skill would further understand that the relative concentration of released bio-oligomer can be affected by varying the cleavage conditions.

Since the beads of the library are immobilized, a concentration gradient of a particular bio-oligomer will form. High concentrations of bio-oligomer will be found in proximity of the bead from which it was released. Thus, evidence of biological activity of interest, in proximity to a bead, will allow identification and isolation of the bead, and sequencing or other characterization of the bio-oligomer. Identification of the bio-oligomer is possible because enough will be left on the bead after partial cleavage for sequencing or other characterization. In another embodiment, the beads may be partitioned in microtiter wells (e.g., 10 beads/well) and a percent of bio-oligomer released and tested for biological activity, thus eliminating the potential problem of diffusion. As described below, different fractions of bio-oligomer may be attached to solid phase support or bead via different cleavable linkers for sequential assays. Within these examples, the term "bead" refers to solid phase support.

The following examples are provided to illustrate how the biological assays may be performed, not as limitations.

(i) A population of cells in single cell suspension is layered over liquid medium or a semi-solid matrix containing a random bio-oligomer library. In one embodiment, this procedure is carried out in 96 well microwell tissue culture plates with one or more beads per well plus the cell suspension. In another embodiment, a barrier matrix or "cookie-cutter" is applied to the suspension of cells and the beads of a library to create individual chambers. A proportion of peptide on each bead is linked with a water cleavable (e.g., diketopiperazine) or photocleavable linker. Sufficient peptide can be released to exert a biological effect while enough peptide still remains linked to the bead for sequencing. The cell suspension may be in solution or may itself be in a semi-solid matrix. After a suitable incubation period, the cell population is examined for growth or proliferation, e.g., by identification of colonies. In another embodiment, the tetrazolium salt MTT (3-(4,5-dimethyl-thazol-2-yl)-2,5-diphenyl tetrazolium bromide) may be added (Mossman, 1983, J. Immunol. Methods 65:55–63; Niks and Otto, 1990, J. Immunol. Methods 130:140–151). Succinate dehydrogenase, found in mitochondria of viable cells, converts the MTT to formazan blue. Thus, concentrated blue color would indicate metabolically active cells. In yet another embodiment, incorporation of radiolabel, e.g., tritiated thymidine, may be assayed to indicate proliferation of cells. Similarly, protein synthesis may be shown by incorporation of $^{35}$S-methionine. Beads releasing peptide which either stimulated or inhibited cell growth would then be recovered and sequenced, with the identified peptide sequences then retested in solution in confirmatory cultures against the indicator cell type.

(ii) In a further embodiment of (i) supra, the beads of a library are distributed into microtiter wells such that each well contains about ten beads. The beads are suspended in solution phase. Sufficient peptide is released from each bead to exert a biological effect while enough peptide remains on the bead for sequencing. The supernatant containing released peptide may be transferred to a replicate plate or left in the wells with the beads. Biological activity, e.g., growth or proliferation of a cell line, is determined. Beads from wells with biological activity are sequenced and each sequence prepared and tested to determine which of the sequences demonstrated biological activity.

(iii) In yet a further embodiment of (ii), supra, bio-oligomers are attached to beads such that about ⅓ of bio-oligomer can be released in a first step, about ⅓ in a second step, and the remaining ⅓ remain on the bead. Sequential release can result from use of two different cleavable linkers, or by limiting the cleavage agent to release only a portion of the bio-oligomer at each step. For the latter, controlled irradiation of a photocleavable linker may be preferred, although carefully timed exposure to a chemical or enzymatic cleavage agent can accomplish partial cleavage. A library of sequentially cleavable bio-oligomers is prepared and distributed in wells of microtiter plates such that each well contains more than about 50, and more preferably from about 50 to about 250, beads per well. The beads are treated so as to cleave about ⅓ of the bio-oligomers. Supernatent is assayed for biological activity in a replicate assay. Beads from wells demonstrating biological activity are then suspended and distributed into wells of a microtiter plate so that each well contains about 1 to 10 beads. The beads are treated to release another ⅓ of bio-oligomer, and the supernatant assayed for biological activity. Beads from wells demonstrating biological activity are isolated and the attached bio-oligomer is sequenced. Where more than one bead is found, all the identified sequences are prepared and individually tested for biological activity. This two step sequential biological assay provides an efficient, powerful method to screen a very large library for bio-oligomers with specific biological activity.

(iv) Stimulation of cytokine release may be assayed by adding a single cell suspension immobilized in a semi-solid matrix, e.g., agarose gel. Where a bio-oligomer of the invention induces release of cytokine, e.g., lymphokine, growth factor, hormone, etc., presence of the cytokine may be detected by activity of an indicator cell line. Specific assays with an indicator cell line may be made as described in (i), supra. In another embodiment, cytokine released by stimulated cells may be blotted on a membrane, e.g., nitrocellulose, and cytokine detected by immunoassay or a receptor binding assay.

(v) In another embodiment, toxicity of a bio-oligomer may be observed. Zones or plaques of no-growth, e.g., of a transformed or cancer cell line layered over a bio-oligomer library, would indicate cytotoxic activity. In a particular aspect, two cell populations in a semi-solid matrix may be layered, one over the other. In this way, a cytotoxic bio-oligomer specific for the target cell, but not cytotoxic for a bystander cell, could be identified. Such an assay would rapidly identify bio-oligomers for use as chemotherapeutic agents. Cytotoxic bio-oligomers include toxic peptides and antisense oligonucleotides.

(vi) Physiologic change may also be assayed. In one embodiment, a myocardial cell suspension is layered over a library. "Beating" of cells stimulated by a bio-oligomer may be observed. In another embodiment, up-regulation of a particular enzyme may be assayed by detecting increase in a specific enzyme activity if a suitable substrate is available, such as a chromogen (e.g., MTT, (i), supra), fluorophore, or chemiluminescent. Alternatively, up-regulation of an enzyme may be detected by an immunological assay. In yet a further embodiment, histological techniques may indicate physiological or morphological changes effected by a bio-oligomer of the library.

(vii) The present invention provides a method to assay activity of a bio-oligomer in a library on polarized cells, e.g., cells with a basolateral and a luminal face. Polar cell cultures may be prepared on a semi-permeable membrane, corresponding to the lumen. A library is added in a semi-solid matrix to the luminal face or the basolateral face. Various effects of a bio-oligomer of the invention may be assayed, such as polar transport, proliferation, intercellular communication, etc. In particular, by labelling the bio-oligomer, e.g., with a radiolabel or a fluorophore, transportable bio-oligomers can be identified. There is a longstanding need in the art for specifically absorbable molecules. In particular, such molecules would be useful for oral or nasal administration of pharmaceuticals, where transport from the luminal surface to the basolateral surface of the epithelium is desired.

Biological assays with uncleaved bio-oligomers are also envisioned. The biological activity of whole bio-oligomer-coated beads may then be screened. In one aspect, a library may be introduced into an animal. Beads of interest may be isolated from a specific tissue. Beads may be isolated that were specifically absorbed after oral, nasal, or cutaneous administration. In a preferred embodiment, such beads are magnetic, or have some other identifying feature, and thus are readily isolated from the tissue.

It will be readily understood by one of ordinary skill that all of the foregoing biological assays apply to bio-oligomers that comprise peptides, oligonucleotides, or peptide-oligonucleotide chimeras. Peptides and peptide analogs are well known as growth promoters, growth inhibitors, and regulatory molecules. Peptides can act as gene regulators by binding to regulatory sequences on a gene, e.g., by agonizing or antagonizing the effects of promotor, enhancer, and regulatory proteins. Similarly, nucleic acids may act as inhibitors, on inducers of gene expression at the level of transcription by (e.g., binding or blocking promoters, enhancers, transcription stop sites, etc.), processing (e.g., by interfering or aiding mRNA processing), and translation. It is well known in the art to use an oligonucleotide or oligonucleotide analog to block translation of a specific MRNA. Any and all of the libraries described in Sections 5.1.–5.3., supra, may be assayed for biological activity.

It will further be understood by one of ordinary skill in the art that any cell that may be maintained in tissue culture, either for a short or long term, may be used in a biological assay. The term "cell" as used here is intended to include prokaryotic (e.g., bacterial) and eukaryotic cells, yeast, mold, and fungi. Primary cells or lines maintained in culture may be used. Furthermore, applicants envision that biological assays on viruses may be performed by infecting or transforming cells with virus. For example, and not by way of limitation, the ability of a bio-oligomer to inhibit lysogenic activity of lambda bacteriophage may be assayed by identifying transfected E. coli colonies that do not form clear plaques when infected.

Methods of the present invention for assaying activity of a bio-oligomer of a random library of bio-oligomers are not limited to the foregoing examples; applicants envision that any assay system may be modified to incorporate the presently disclosed invention. Applicants envision that such are within the scope of their invention.

5.5.2.1. BIOASSAY FOR A ERYTHROPOIETIN AGONIST

In a particular embodiment, the present invention provides an assay for a bio-oligomer agonist of erythropoietin. It should be recognized that the particular method described herein would provide a useful strategy for identifying any agonist, e.g., agonist of growth factors, hormones, cytokines, lymphokines, and other intercellular messengers, such as are described in Section 5.5.2., supra.

In the present example, the bio-oligomer library may consist of pentapeptides prepared with the 19 common amino acids (excluding cystine). The theoretical number of distinct peptides is 2,476,099. The library may be produced in 19 stages to facilitate the screening effort. This will be accomplished by selecting a single amino acid for the C-terminal at each stage so that only the other four amino acid positions will be randomized. Thus, the sequence for each stage will be XXXXY-linker-resin, where Y is selected for that stage and X represents random amino acid incorporation. This approach reduces the number of potential peptides for each stage to 130,321. Distributed as 10 beads (peptides) in each well of 96 well microtiter plates, the number of plates required is 136 (one additional plate is required for bioassay standards and controls to give a total of 137). The method allows the distribution of the entire stage of the library over this number of plates in one working day.

A major portion (50–80%) of the peptide synthesized on the beads can be cleaved for use in the bioassay so that at least 50 pmol of peptide will be consistently released from each bead. A diketopiperazine linkage is preferred as the cleavable linker, although a photoclevable linker may also be used. The linkage is sufficiently stable under mild acid conditions (e.g., 0.1–1.0 mM HCl) to allow the distribution of the beads over a 6–8 hour period. Cleavage is promoted by the addition of 20 µl of 1.0–10 mM HEPES buffer (pH 8.5) to each well. Cleavage occurs overnight (12–18 hours) consistent with the maintenance of the final well volume. Evaporation can be controlled by storing the plates in a humidified chamber.

The peptide solution resulting from the cleavage of the library beads should be aseptic if not actually sterile. Aseptic conditions are necessary because the solution will comprise 25% of the final culture volume and because the culture time will be at least 24 hours. Aseptic conditions can be achieved by (1) hydrating the beads in sterile water after synthesis, (2) diluting the initial bead suspension in acidified sterile water and (3) using sterile technique to distribute the beads into sterile culture plates. The final bead suspension may contain less than about 20% DMSO to help solubilize hydrophobic peptides. The DMSO should be added, if at all, early in the hydration process to facilitate solubilization. The final bead suspension should yield a concentration of 10 beads/50 µl. Maintaining the beads in suspension during the pipetting may be accomplished by the addition of methyl cellulose to about 0.8–3.2%. The use of methyl cellulose may allow the reduction of the DMSO used to promote solubility. Methyl cellulose final concentration in the cultures is kept below 0.8% so as not to interfere with the bioassay.

The released peptides can be transferred to bioassay culture plates as 50 µl samples, maintaining an exact correspondence between sample plates and culture plates. It is important that sterile conditions be maintained during this transfer. Human recombinant EPO can be added to selected wells of the plates to serve as a positive. control (each plate) and for the construction of standard curves (first and last plates). Control wells may receive 0.1 IU EPO, and standard curves obtained from six sets of duplicate wells receiving 1.0–100 milliunits EPO (D'Andrea, et. al. 1991, Mol. Cell Biol. 11:1980–1987).

The bioassay can be made with the Ba/F3-T recombinant cell line expressing erythropoietin receptor (EPO-R). These cells are dependent on the presence of either interleukin-3 (IL-3) or EPO. Culture of these cells in the presence of IL-3 (supplied as 10% (v/v) WEHI-conditioned culture medium) will prevent the possible interference of EPO in the medium with the bioassay. Basic growth medium for Ba/F3-T cells is RPMI 1640 medium containing 2.0 g/L NaHCO$_3$ 10% (v/v) fetal bovine serum, 1×penicillin-streptomycin, 5 µl β-mercaptoethanol/L and 10 mM HEPES (final concentration) adjusted to pH 7.40. This medium must be supplemented with 10% (v/v) WHEI-conditioned medium, which supplies IL-3. WHEI-conditioned medium is prepared by culturing WHEI cells to confluence in the same basic medium. The conditioned medium is centrifuged to remove cells, passed through a 0.22 µm filter and stored frozen. The Ba/F3-T cells are cultured to give 1.31×10$^7$ cells, which will be distributed as 1×10$^3$ cells/well in a volume of 150 µl as described (Yoshimura et al., 1990, Proc. Natl. Acad. Sci. U.S.A. 87:4139–4143).

The Ba/F3-T cells are transferred from roller bottles to large (250 ml) sterile centrifuge bottles. The cells will be collected by centrifugation at about 500×g for 5 minutes. The cells are then resuspended in 200 ml fresh basic medium without IL-3 for cell counting. The final volume is then adjusted to give 6.67×10$^3$ cells/ml (1×10$^3$ cells/150 µl) with additional medium. It will be necessary to divide the final cell suspension into 4–8 aliquots for storage in the incubator during the long distribution process. Cell number and viability should be determined on samples taken at the beginning and end of the distribution process to insure that similar numbers of viable cells are present in the first and last culture plates. The cells are distributed into the culture plates containing the released peptide supernantants. The plates are incubated for three days (Yoshimura, et al., supra).

The endpoint of the bioassay is the number of live cells present in each culture well. This may be determined using the MTT assay of Mosmann (1983, J. Immunol. Methods 65:55–63) as modified by Niks and Otto (1990. J. Immunol. Methods 130:140–151). The modified assay allows the measurement of living cell number without removing the culture medium.

MTT ((3(4,5-dimethylthiazol-2-yl)2,5-diphenyl tetrazolium bromide) is prepared as a 5 mg/ml solution in PBS (about 270 ml required). Each well of the bioassay plate receives 20 μl of this solution, and the plate is incubated for 4 hours at 37°. Following this period, 100 μl of extraction solution are added to each well and the plate is placed in a bath sonicator for 120 seconds. The extraction solution comprises 50% (v/v) N,N-dimethylformamide in a 20% (w/v) solution of sodium dodecylsulfate (SDS) adjusted to pH 4.7 with acetic-HCl acid as described by Hansen et al. (1989, J. Immunol. Methods 119:203). This treatment solubilizes the formazan product of MTT metabolism for measurement of the optical density at 570 nm by a microplate reader.

The OD data obtained from the bioassay is averaged over all sample wells to determine a 95% confidence interval for the mean value. OD values for wells outside this interval are used for a Students t test determination of significance. Significant values will be compared to the EPO standard curve to obtain a potency estimate as IU relative to EPO. The standard curve is determined by nonlinear regression analysis using the logistic equation. Data from both standard curves will be analyzed together and separately to determine if there is a significant difference in the response measured at both ends of the bioassay procedure (F-ratio test). A comparison of control values measured for each plate over the entire assay will be used to determine if there is a consistent change in the assay response.

It is important to recognize that there are two growth factor receptors (IL-3R and EPO-R) present on the Ba/F3-T cells and that activation of either will produce a positive bioassay response. Thus, the bioassay as described above will select for both IL-3 and EPb receptor agonists. There are two solutions to this problem. One is to use a different cell line or perhaps spleen cells from phenylhydrazine treated mice (Krystal, 1983, Exp. Hematol. 11:649–660). A second is to test synthetic peptides for both EPO and IL-3 activity in a second bioassay or by radioligand binding methods.

5.5.3. ENZYME MIMICS/ENZYME INHIBITORS

The present invention further comprises bio-oligomers that catalyze reactions, i.e., enzyme libraries, that serve as co-enzymes, or that inhibit enzyme reactions. Thus, the invention provides methods to assay for enzyme or co-enzyme activity, or for inhibition of enzyme activity.

Enzyme activity may be observed by formation of an detectable reaction product. In a particular embodiment, a bio-oligomer of a library catalyzes the enzyme reaction of alkaline phosphatase substrate, e.g., 5-bromo-4-chloro-3-indolyl phosphate (BCIP) and forms a blue, insoluble reaction product on the solid phase support (see Example 13, infra).

In another embodiment, a zone of observable product, e.g., color or fluorescence, may be formed in a semi-solid matrix. A library is layered in a semi-solid matrix, e.g., agarose gel, and a chromogenic or other indicator substrate is added. Where a bio-oligomer/solid phase support shows the desirable enzyme activity, a zone of product will form. For example, and not by way of limitation, a bio-oligomer analog of horseradish peroxidase may be identified by adding a solution of aminoantipyrene (0.25 mg/ml; Kodak), phenol (8 mg/ml) and $H_2O_2$ (0.005%) in 0.1M phosphate buffer, pH 7.0. Beads with enzyme activity will form a purple zone of color. In another embodiment, bio-oligomers/beads with protease activity may be identified by addition of the well known calorimetric protease substrates.

Co-enzyme activity may be observed by assaying for the enzyme activity mediated by a co-enzyme, where the natural or common co-enzyme is absent.

Enzyme inhibitory activity can be detected with a partially-released bio-oligomer. Release of bio-oligomers is discussed in Sections 5.4. and 5.5.2, supra. In one example, and not by way of limitation, a bio-oligomer library is layered in a semi-solid matrix that contains an enzyme. The library is treated to partially release bio-oligomer. Where the bio-oligomer inhibits the enzyme activity, a zone lacking product may be identified. In one embodiment, the enzyme substrate is chromogenic, and a colored product is formed. Thus, presence of an enzyme inhibitor would yield a zone of no color. In another embodiment, inhibition of a proteolysis of hemoglobin or an indicator enzyme such as alkaline phosphatase may be detected by the presence of an opaque zone in the semi-solid matrix. This is because presence of proteolysis inhibitor will prevent degradation of the hemoglobin or indicator enzyme.

It will be well known to one of ordinary skill that a bio-oligomer that demonstrates enzyme activity, co-enzyme activity, or that inhibits enzyme activity, may be a peptide, an oligonucleotide, or a peptide-oligonucleotide chimera. Of particular interest are the constrained or circularized peptides, which can create an unique catalytic binding pocket or surface (Section 5.2.1., supra). Also, a peptide-oligonucleotide chimera may be expected to exhibit unique chemical properties, such as enzyme or co-enzyme activity, due to the unique juxtaposition of the respective functional groups. Furthermore, it is envisioned that the bio-oligomer/solid phase support may demonstrate enzyme or co-enzyme activity, while the free bio-oligomer may have no activity. This is because proximity of a high density of bio-oligomer may confer unique chemical properties to the bio-oligomer/solid phase support. It is also envisioned that a bio-oligomer may exhibit enzyme or co-enzyme activity when released from the bead. It is envisioned that known coenzymes (cofactors) may be chemically incorporated into the constrained bio-oligomer to simulate a simple or complex enzyme including, e.g., an electron transport chain.

5.6. METHODS OF CHARACTERIZING A BIO-OLIGOMER

Once a bead containing a bio-oligomer of interest is selected according to any one of the methods of Section 5.5.1 supra, the present invention provides a means of determining the structure and the sequence of the bio-oligomer.

Where the bio-oligomer is a peptide, the preferred sequencing method is Edman degradation. A particularly preferred method employs the Applied Biosystems 477A Protein Sequencer. The amino acid sequence of peptides can also be determined either by fast atom bombardment mass spectroscopy (FAB-MS) or with other analytical methodologies.

The peptides can be sequenced either attached to or cleaved from the solid support. To cleave the peptide, the isolated peptide-beads are treated with traditional cleaving agents known to those of skill in this art to separate the polymer from the solid phase supports. The choice of cleaving agent selected will depend on the solid phase support employed. For example, to cleave peptides off of the Wang resin, it is preferred to use 50% trifluroacetic acid (TFA) in dichloromethane.

Alternatively, in another embodiment within the scope of the invention, it is possible to isolate a single solid phase support, such as a bead, with its attached bio-oligomers and apply the bead to a sequencer without previously cleaving the bio-oligomers from the bead. For example, if the bio-oligomers is a peptide, it is estimated that a single 100 μm diameter resin with 0.5 mEq/gram resin substitution contains approximately 200 pmole of peptide. A single 250 μm diameter PAM resin with 0.5 mEq/gram resin substitution contains approximately 3125 pmole of peptide. With state of the art peptide sequencer, only 5–10 pmole is required for adequate sequencing. Therefore, one standard size, single PAM resin support of 100 μm diameters contains more than an adequate amount of peptide for sequencing.

In the case where peptides comprise amino acids or peptidomimetics that are not amenable to Edman analysis, the bead may be prepared such that 10–50% of the peptides do not incorporate the unsequencable residue. The remaining sequence may be determined, and the sequence including the unsequencable residue extrapolated therefrom.

Another approach for unsequenceable residues is to temporarily cap a portion of the peptide prior to incorporation of the unsequenceable residue during the synthesis of the library. During the subsequent structural identification, one may use Edman degradation up to the unsequenceable residue, then deprotect the temporary cap and resume sequencing distal (i.e., C-terminal) to the unsequenceable residue.

In the case of oligonucleotides, sequencing may be performed on an automated oligonucleotide sequencer (e.g., Applied Biosystems). A preferred alternative is to use the technique of Maxam and Gilbert (1977, Proc. Natl. Acad. Sci. U.S.A. 74:560–564). Other methods of sequencing oligonucleotides known in the art may also be used.

Fast ion bombardment mass spectrometry provides perhaps the most powerful structural analysis. By detecting fragments as well as the bio-oligomer species itself, a sequence may be reconstructed. Electrospray-high performance mass spectrometry (Finnigan MAT) can provide structural and sequence data as well.

Once the sequence of the selected bio-oligomer is determined, a large amount can be synthesized chemically using an automatic peptide synthesizer or other means of bio- or chemical synthesis. In addition, once a bio-oligomer sequence has been identified, subunit analogs may be substituted to enhance the activity of the specific bio-oligomer.

5.7. THERAPEUTIC AND DIAGNOSTIC AGENTS FROM RANDOM BIO-OLIGOMER LIBRARIES

Once a bio-oligomer sequence of interest has been determined, the present invention provides molecules that comprise the bio-oligomer sequence for use in treatment or diagnosis of disease. The sequence of the bio-oligomer alone may provide a diagnostic or therapeutic agent, or may be incorporated into a larger molecule. A molecule comprising a bio-oligomer sequence with biological or binding activity may be termed an "effector molecule." The invention further provides libraries for use in various applications. The "effector" function of said effector molecule may be any of the functions described herein or known in the art.

The method described herein not only provides a new tool to search for specific ligands of potential diagnostic or therapeutic value, but also provides important information on a series of ligands of potentially vastly different primary sequence or chemical composition which nontheless are able to interact physically with the same acceptor molecule. Integrating such information with molecular modeling and modern computational techniques is likely to provide new fundamental understanding of ligand-receptor interactions.

The therapeutic agents of the invention comprise effector molecules that will bind to the biologically active site of cytokines, growth factors, or hormonal agents and thereby enhance or neutralize their action, and that will block or enhance transcription and/or translation.

The therapeutic agents of the invention include, for example, effector molecules that bind to a receptor of pharmacologic interest such as growth factor receptors, neurotransmitter receptors, or hormone receptors. These effector molecules can be used as either agonists or antagonists of the action of the natural receptor ligand.

Another application of effector molecules that bind to receptors would be to use the binding to block the attachment of viruses or microbes that gain access to a cell by attaching to a normal cellular receptor and being internalized. Examples of this phenomenon include the binding of the human immunodeficiency virus to the CD4 receptor, and of the herpes simplex virus to the fibroblast growth factor receptor. Effector molecules that occupy the receptor could be used as pharmacologic agents to block viral infection of target cells. Parasite invasion of cells could be similarly inhibited, after suitable effector molecules were identified according to this invention.

In another embodiment, an effector molecule comprising a bio-oligomer sequence that binds to an acceptor molecule of interest may be used to target a drug or toxin. In a preferred embodiment, the acceptor molecule of interest is a receptor or antigen found on the surface of a tumor cell, animal parasite, or microbe, e.g., bacterium, virus, unicellular parasite, unicellular pathogen, fungus or mold.

In addition, it is possible that a few of the millions of bio-oligomers in the pool may provide sequences that have biological activity, one may isolate bio-oligomers that possess antitumor, anti-animal parasite, or antimicrobial, e.g., antifungal, antibacterial, anti-unicellular parasite, anti-unicellular pathogen, or antiviral activities. In addition some of these bio-oligomers may act as agonists or antagonists of growth factors, e.g., erythropoietin, epidermal growth factor, fibroblast growth factor, tumor growth factors, to name but a few, as well as hormones, neurotransmitters, immunomodulators, or other regulatory molecules. In one embodiment, the bio-oligomers are peptides.

The therapeutic agents of the invention also include effector molecules comprising a bio-oligomer sequence that has a high affinity for drugs, e.g., digoxin, benzodiazepam, heroine, cocaine, or theophylline. Such peptides can be used as an antidote for overdoses of such drugs. Similarly, therapeutic agents include effector molecules that bind to small molecules or metal ions, including heavy metals. Bio-oligomer sequences with high affinity for bilirubin will be useful in treatement of neonates with hyperbilirubinemea.

In general, the present invention envisions providing methods to identify bio-oligomer sequences for therapy of diseases or illnesses such as are listed in the Product Category Index of The Physicians Desk Reference (PDR, 1991, 45th Edition, Medical Economics Data: Oradell, N.J., pp. 201–202). For example, an effector molecule with antiparasite, anticoaguluant, anticoagulant antagonist, antidiabetic agent, anticonvulsant, antidepressant, antidiarrheal, antidote, antigonadotropin, antihistamine, antihypertensive, antiinflammatory, antinauseant, antimigraine, antiparkinsonism, antiplatelet, antipruritic, antipsycotic, antipyretic, antitoxin (e.g., antivenum), bronchial dilator, vasodilator, chelating agent, contraceptive, muscle relaxant, antiglaucomatous agent, or sedative activity may be identified.

The therapeutic agents of the invention may also contain appropriate pharmaceutically acceptable carriers, diluents and adjuvants. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the patient. While intravenous injection is a very effective form of administration, other modes can be employed, such as by injection, or by oral, nasal or parenteral administration.

A molecule comprising a bio-oligomer sequence determined according to this invention may also be used to form diagnostic agents. The diagnostic agent may be made up of one or more bio-oligomer sequence of the instant invention, e.g., more than one peptide sequence or oligonucleotide sequence. In addition, the diagnostic agent may contain any of the carriers described above for therapeutic agents.

As used herein, "diagnostic agent" refers to an agent that can be used for the detection of conditions such as, but not limited to, cancer such as T or B cell lymphoma, and infectious diseases as set forth above. Detection is used in its broadest sense to encompass indication of existence of condition, location of body part involved in condition, or indication of severity of condition. For example, a peptide-horseradish immunoperoxidase complex or related immunohistochemical agent could be used to detect and quantitate specific receptor or antibody molecules in tissues, serum or body fluids. Diagnostic agents may be suitable for use in vitro or in vivo. Particularly, the present invention will provide useful diagnostic reagents for use in immunoassays, Southern or Northern hybridization, and in situ assays.

In addition, the diagnostic agent may contain one or more markers such as, but not limited to, radioisotope, fluorescent tags, paramagnetic substances, or other image enhancing agents. Those of ordinary skill in the art would be familiar with the range of markers and methods to incorporate them into the agent to form diagnostic agents.

The therapeutic agents and diagnostic agents of the instant invention may be used for the treatment and/or diagnosis of animals, and more preferably, mammals, including humans, as well as mammals such as dogs, cats, horses, cows, pigs, guinea pigs, mice and rats. Therapeutic or diagnostic agents may also be used to treat and/or diagnose plant diseases.

The diseases and conditions amenable to therapy or diagnosis with bio-oligomers discovered according to the present invention are as varied and wide-ranging as the permutations of structures in a random bio-oligomer library. The following examples are provided for purposes of illustration and not limitation.

5.7.1. CYTOTOXIC COMPOSITIONS

A molecule comprising a bio-oligomer sequence may have specific cytotoxic activity on its own. Also a bio-oligomer that binds an acceptor of interest may be modified by techniques that are within the routine skill of the art such as, for example, by conjugation to cytotoxic compounds, such as drugs or radionuclides, to create a cytotoxic molecule. The bio-oligomer, e.g., peptide, can "target" the cytotoxic compound and specifically destroy cells displaying a particular acceptor molecule. For example, such cytotoxic peptide conjugates could directly eliminate unwanted B cell populations, B cell lymphomas, T cell populations, or T cell lymphomas in a patient. The potential clinical applications include treating autoimmune diseases, lymphomas, and specific immunosuppressive therapy for organ transplantation. Other forms of cancer where the tumor cells-exhibit receptor mediated binding of ligand, such as breast or ovarian cancer where epidermal growth factor (EGF) receptors are believed to play a role, could also be treated in this fashion.

Cytotoxic agents specific for a target cell, such as a cancer cell or virally infected cell, but that do not kill bystander cells, tissues or organs, may be obtained according to the instant methods. In addition to targeting detrimental cells such as tumors, these specific toxins may be useful antimicrobial agents. In particular, such therapeutic agents may exhibit bacteriostatic, bacteriocidal, antiviral, anti-parasite, or fungicidal activity. Similarly, toxins may be identified that have insecticidal or herbicidal activity.

In one embodiment, the bio-oligomer may be a peptide. The peptide may act as a targeting agent, to which a toxin is attached. The peptide itself may target a cell, and act as a toxin. In another embodiment, the bio-oligomer may be an oligonucleotide. The oligonucleotide may mediate its toxic effect by interfering with transcription or translation essential for cell viability.

5.7.2. IMMUNE MODIFIERS

The present invention provides molecules and compositions for use as immune modifiers. The term "immune modifier" comprises molecules or compounds capable of effecting changes in the immune system. In particular, immune modifiers can stimulate or inhibit T cell responses, B cell responses, and non-specific immune responses such as are mediated by the action of macrophages, neutrophils, polymorphonuclear phagocytes, granulocytes and other myeloid lineage cells. Effector molecules may be used to treat the following immune conditions: (1) various autoimmune diseases including myasthenia gravis, multiple sclerosis, Grave's disease, rheumatoid arthritis, systemic lupus erythematosis (SLE), Pemphigus Vulgaris, autoimmune hemolytic anemia, and immune thrombocytopenia, (2) non-Hodgkin's lymphoma and various other cancers, (3) allergy, (4) immune complex diseases, (5) transplant organ rejection, (6) infectious disease, and (7) diabetes mellitus.

The immune modifier may stimulate immune activity by mimicking the activity of a stimulatory lymphokine such as interleukin (IL-)-1, IL-2, IL-4, IL-6, granulocyte-colony stimulating factor (CSF), macrophage-CSF, and granulocyte/macrophage-CSF, to mention but a few. Stimulation may occur by peptide binding of ligand to a lymphokine receptor, or by oligonucleotide mediating activation of the cellular transcriptional machinery. An immune modifier may act by binding to a leukocyte or lymphocyte such as F, receptor, LAF-1, LAF-2, etc., and inducing activity such as phagocytosis or release of cytotoxins. An effector molecule of the invention may act as a chemotaxin.

In a particular embodiment, a molecule comprising a bio-oligomer may mimic antigen. As such the bio-oligomer may be a useful vaccine to elicit T cell or B cell activity specific for a particular pathogen. Alternatively, an antigen, i.e., epitope, mimic would have use in boosting a specific immune response.

It is envisioned that the effector molecules of the invention will be effective in released form. However, a particular bio-oligomer may demonstrate greater effectiveness when it remains bound to a solid phase support. In particular, the high density of epitope mimic may more effectively stimulate a B cell response by binding and capping membrane immunoglobulin, or other receptor-mediated response.

It is further envisioned that a limited library of the invention may be useful as a vaccine for a pathogen that presents with a diversity of epitopes. For example, it is known that the primary structure (sequence) of VSG (variable surface glycoprotein) of trypanosome varies over time during infection. By altering the VSG epitope, trypanosome evades immune recognition. Similarly, malarial parasites are found to express diverse antigenic epitopes across species, at different stages of the life cycle, and within subspecies. Thus a peptide library of restricted diversity could immunize against the variable antigenic diversity presented by trypanosome or malarial parasites. A limited library may have application as a vaccine in any case where immunity to a range of antigens is desired.

It is envisioned that the effector molecules may also inhibit immune response by (i) blocking specific immune recognition at the level of antibody or the T cell antigen receptor; (ii) by blocking F, or other immune receptors; or (iii) binding to and inhibiting the activity of lymphokines and cytokines; (iv) by providing negative feedback signals to immune cells. Effector molecules may be used to tolerize the immune system, in particular to autoimmune antigens. For example, immune tolerance to DNA could be effected with an oligonucleotide or oligonucleotide library, and may be useful in the treatment of SLE. Furthermore, immune inhibition may be affected by the mechanisms described in Section 5.7.1., supra.

In addition, the therapeutic agents of the invention may include selected synthetic antigenic peptides with which it would be possible to manipulate the immune system so as to induce tolerance to that antigen and hence suppress or cure the corresponding autoimmune disease. Similarly, with specific synthetic antigenic peptides, it is possible to inhibit the formation of multimeric immune-complexes, and hence prevent specific immune-complex diseases.

Peptides that bind to tumor-specific monoclonal antibodies could be isolated, sequenced and synthesized for use as an immunogen to induce active immunity against the tumor.

Specific peptides that have high affinity to Fc receptors could be used as therapeutic agents to block the Fc receptors of the reticuloendothelial system, which would be potentially beneficial for patients with autoimmune diseases such as idiopathic thrombocytopenia and autoimmune hemolytic anemia.

The potential for treatment with such peptides may be even more significant. Peptides that resemble epitopes of invading organisms may be used to block infection by an organism. For example, recent studies on Acquired Immune Deficiency (AIDS) have shown that the infection by the AIDS virus begins with recognition and binding between a specific glycoprotein (gp120) on the envelope of the AIDS virus and the CD4 surface receptor on the cell. Administering a peptide that resembles gp120 may sufficiently block the CD4 receptor so that the AIDS virus will not be able bind to and infect that cell. Similarly, parasite invasion and infection may also be inhibited.

5.7.3. NEUROACTIVE AGONISTS AND ANTAGONISTS

It is envisioned that effector molecules of the present invention will agonize (mimic) or antagonize (inhibit) the effects of hormones, neurotransmitters, analgesics, anesthetics, anti-psychotics, anti-depressants, or narcotics. Such effector molecules would be useful in the discovery of appetite regulators, psychiatric drugs, attention and learning modulators and memory aids. The present invention further provides a source of taste and scent analogs, e.g., "artificial" sweetener, salt, and scents.

5.8. LIMITED LIBRARIES

It is further envisioned that a limited library of the invention may provide a complex flavor, e.g., like a spice, at lower cost or without the occasional allergic effects of flavorings. In this way expensive flavors like saffron may be replaced. In another aspect, a new class of flavorings may be created.

In another embodiment, a limited library may provide a unique chromatographic support. It is envisioned that a library of bio-oligomers, e.g., peptides that share general chemical properties but having a variety of sequences, would be more useful chromatographic support than are presently available. Such a chromatographic support would be more selective than an ion exchange or reverse phase support. Yet an acceptor molecule to be purified could be eluted from the support readily under much gentler conditions than are possible using, for example, an immunoaffinity support, thus decreasing the likelihood of denaturation. In one embodiment, a support may be prepared based on composition or structure of bio-oligomers that were found to be of intermediate affinity, e.g., intermediate labeling intensity, or only bound at a high concentration of specific acceptor molecule. Furthermore, a highly selective, lower stringency support could be rapidly identified without purified material (see Section 5.5.1., supra).

In another embodiment, low affinity-binding beads may be selected, and a limited library prepared based on composition of the selected beads. In another embodiment, a custom low affinity or high affinity support comprising one or a few bio-oligomer sequences identified from the millions of sequences provided by the invention may be used for chromatography.

The invention will be further clarified by the following examples, which are intended to be purely exemplary of the invention.

6. EXAMPLE

SYNTHESIS OF A TETRAPEPTIDE LIBRARY

The method of the invention was used to synthesize a tetrapeptide family of the formula X-X-X-Trp where X can be either a valine, a serine or an alanine and the first amino acid is always a tryptophan. Tryptophan has been incorporated at the carboxyl terminus to facilitate spectrophotometric monitoring at $OD_{280}$.

$N^\alpha$-Fmoc-tryptophan-alkoxymethyl polystyrene resin as described in Wang (1973, J. Amer. Chem. 95:1328–1333) was obtained from Bachem Inc., Torrence, Calif., and placed into a standard solid phase peptide synthesis vessel. The amino acids to be added were also the Fmoc-modified amino acids obtained from Bachem Inc. The other reagents used are essentially the same as those routinely used in the solid phase synthesis are those set forth by Austen, (1988, "Peptide Synthesis" Methods in Molecular Biology, vol. 3 pp.311–331).

Reaction vessels with Teflon™ lining caps were used for the coupling reactions; a standard solid phase protein synthesis reaction vessel served as the mixing chamber into which the aliquots were mixed after the coupling reaction.

Approximately 0.5 grams of Fmoc-Trp alkoxymethyl resin were swollen with 20 ml of dichloromethane (DCM). The resin was then washed twice with DCM, once with a 1:1 mixture of DCM and dimethylformamide (DMF), and three times with DMF. The resin was then deprotected with 20% (v/v) piperidine in DMF. After thorough washing of the deprotected resin with DMF (3 times), DCM (3 times), and 1:1 mix of DCM and DMF (2 times), the resin was resuspended in approximately 7.5 ml of DMF, and divided into three separate aliquots of approximately 2.5 ml each and distributed into three numbered coupling tubes.

The quantity of protected amino acid to be added calculated based on the number of moles of tryptophan already attached to the resin. For each amino acid to be added, a five-fold molar excess of the amino acid was added into each reaction vessel into which the washed resin had already been aliquoted. Each reaction vessel received a five-fold excess of different amino acid. Each vessel was shaken for two minutes, and a five-fold molar excess of diisopropylcarbodiimide (DIC) in 3 ml of DCM was added, followed by 1 hour of shaking.

To test for completeness of coupling, a sample from each tube was tested with ninhydrin reagent obtained from Pierce Chemical in the method set forth by Sarin et al. (1981, Anal. Biochem. 117:147–157), specifically incorporated herein by reference. If the coupling reaction was incomplete as determined by this test, the reaction was forced to completion by several methods familiar to those in the art, including (a) a second coupling using a one- to five-fold excess of protected amino acid, (b) an additional coupling using different or additional solvents (e.g., trifluoroethanol), or (c) the addition of chaotropic salts, e.g., $NaClO_4$ or LiBr (Klis and Stewart, 1990, "Peptides: Chemistry, Structure and Biology," Rivier and Marshall, eds., ESCOM Publ., p. 904–906).

After coupling, the resins from the three coupling tubes were carefully transferred and combined in the single mixing chamber. The resin was washed 2 times with DCM/DMF (1:1), 3 times with DCM, 3 times with DMF, and deprotected with 20% (v/v) piperidine/DMF. After thorough washing with DCM and DMF as described above, the mixture was divided into three aliquots and distributed into the three separate reaction vessels. A second set of amino acids was added. After coupling was complete, the resin was first deprotected with 20% piperidine followed by thorough washing with DCM and DMF as described above. A third set of amino acids were added in the same way.

To cleave the peptides from the solid phase supports, 30 ml of 50% (v/v) trifluoroacetic acid (TFA) plus 5% (v/v) anisole and 0.9% (v/v) ethanedithiol in DCM were added to the resin. The mixture was shaken for four hours and the peptide supernatant was collected. The peptide supernatant was then concentrated by a rotary evaporator and the peptides were precipitated in ether. After a thorough washing, the peptide precipitate was dried and ready to be used for further analysis. The lyophilized peptide (in powder form) was stored frozen.

7. EXAMPLE

COMPARISON OF THE CLAIMED METHOD WITH THE CONVENTIONAL METHOD OF PEPTIDE SYNTHESIS

7.1. MATERIALS AND METHODS

A library of random tetrapeptides was produced in accordance with Example 6 above. In addition, a library of tetrapeptides was produced using the standard solid phase peptide synthesis (hereinafter "SPPS") techniques set forth in Austen, supra. $N^{\alpha}$-Fmoc-Tryptophan-alkoxymethyl resin, obtained from Bachem, Inc., was used as the solid phase support/amino acid combination. Equimolar quantities of a five-fold excess of $N^{\alpha}$-Fmoc-valine, $N^{\alpha}$-Fmoc-serine (O-$^t$Bu), and $N^{\alpha}$-Fmoc-alanine were added into the reaction vessel during each coupling step. After three consecutive coupling steps, the tetrapeptides were cleaved in 50% (v/v) TFA, 5% (v/v) anisole, and 0.9% (v/v) ethanedithiol in DCM as described in Austen, supra.

7.2. RESULTS

Both peptide libraries were analyzed on a C-18 reverse phase HPLC chromatography column (Vydac) to demonstrate the number of peptide species in the library (number of peaks), relative concentration of peptides (area of peaks), and relative hydrophilic nature of peptides (early or late elution from the column). The results are set forth in FIG. 1. The chromatogram in the upper panel (FIG. 1A) reflects the pattern obtained with the library of peptides prepared according to the method of the invention and the chromatogram in the lower panel (FIG. 1B) reflects the pattern obtained with SPPS.

Both patterns exhibit 21 distinct peaks, indicating the presence of at least 21 different peptide species within each library. The SPPS pattern, however, exhibits significantly greater peaks at # 1, 2, 3, 4, 5, 6, and 7, indicating that the SPPS library contained a greater concentration of peptides 1–7 than of peptides 8–21. The increased number of peptides 1–7 demonstrates that these peptides were preferentially synthesized over the rest of the 21 peptides. In addition, these prominent peaks were eluted early, that is, these peptides exhibited a shorter retention time within the column, indicating that the peptides were more hydrophilic in nature.

This result is not unexpected with the SPPS system. It is known in the art that valine is hydrophobic and bulky and has a significantly slower coupling rate (believed due to steric hinderance) than that found with either alanine or serine. Thus, during a conventional random peptide synthesis as conducted here, in which valine essentially "competes" with alanine and serine for coupling sites, the peptides synthesized were valine-poor and the peptide library produced did not exhibit an equimolar distribution of the random peptides.

In contrast, the pattern of the library of random peptides produced according to the method of the invention did indicate an equimolar distribution of peptides. Although peaks 3, 6, 12, 13 and 18 were approximately twice the area of other peaks, indicating the presence of two peptides at that point, most of the remaining 16 peaks have almost identical patterns. In addition, all 21 peaks span the range of retention time, also indicating an equimolar distribution of peptides.

Sequencing of selected peaks provided further support. Smaller peaks 8, 9, and 21 and large peak 6 were sequenced with an Applied Biosystems 477A Protein Sequencer:

8=Val-Ala-Ser-Trp
9=Val-Ser-Ala-Trp
21=Val-Val-Val-Trp
6=(Ser-Val)-(Ser-Ala)-(Ser-Ala)-Trp

These valine-containing sequences confirm that the method of the invention does permit the random synthesis of peptides even when known slow-coupling amino acids are used.

The sequence for peak #6 was not conclusive, apparently due to the presence of more than one peptide under the peak. Most likely the two major peaks are Ser-Ala-Ala-Trp and Val-Ser-Ser-Trp.

7.3. CONCLUSION

The results demonstrate that the random peptide synthesis method of the invention permits the synthesis of a library of random peptides in substantially equimolar amounts, in contrast to standard SPPS technique, in which a set of peptides that contains amino acids with a faster coupling rate predominate.

8. EXAMPLE

ISOLATION OF A PEPTIDE LIGAND THAT BINDS TO A RECEPTOR MOLECULE

To demonstrate the use of the method of the instant invention to isolate a particular peptide, a 12 amino acid peptide with the predetermined sequence from the V-mos gene product was synthesized. V-mos is an oncogene isolated from mouse sarcoma, and is related to the Moloney murine sarcoma virus. The v-mos gene product is known to have serine/threonine kinase activity.

8.1. MATERIALS AND METHODS

The sequence, Leu-Gly-Ser-Gly-Gly-Phe-Ser-Val-Tyr-Lys-Ala, was synthesized on polyacrylamide bead (~300 μm diameter) using $N^\alpha$-Fmoc chemistry and standard solid phase peptide synthesis reagents and techniques. The side chain protecting groups were removed by 50% TFA, and the peptide remained covalently linked to the polyacrylamide resin via a linker, aminocaproic acid-ethylenediamine, to yield a final structure: Leu-Gly-Ser-Gly-Gly-Phe-Ser-Val-Tyr-Lys-Ala-aminocaproic acid-ethylenediamine resin (hereinafter "long v-mos bead"). This peptide sequence corresponds to residues 100 to 111 of the v-mos gene product.

Using the same method, a shorter peptide of residue 106-111 of the v-mos gene product (Gly-Ser-Val-Tyr-Lys-Ala) was synthesized on the polyacrylamide bead via the same linker (hereinafter "short v-mos bead"). This peptide served as a negative control.

A hybridoma cell line producing mouse monoclonal antibody specific against the long v-mos peptide, known as anti-v-mos (Hybridoma No. 165-28E7, SCRF 354, Lot No. 165-119), was obtained commercially from Microbiological Associates Inc., Maryland. In ELISA testing, this antibody detects homologous sequence of v-mos, MOS, neu/HER-1, HER-2 gene products. This antibody is known to have negligible affinity to the short v-mos peptide. A secondary goat-anti-mouse IgG (heavy and light chain specific) labeled with alkaline phosphatase was obtained from Sigma.

Using conventional techniques for the production of monoclonal antibody as set forth in *Methods in Enzymology*, Vol. 121 (1986), monoclonal antibodies were produced in the form of ascites, and subsequently purified on a protein G-column obtained from Pharmacia.

8.2. RESULTS

The long v-mos beads were mixed with a thousand fold excess of the short v-mos beads. Two milliliters of the purified anti-v-mos monoclonal antibody (1 μg/ml) in PBS with 0.1% Tween 20 was added to the mixture of long and short v-mos beads and incubated at room temperature for one hour with gentle mixing. The beads were then washed for one hour with gentle mixing. The beads were then washed on a small polypropylene disposable column (obtained from Isolab) where the beads were retained by the frit. The beads were then mixed with 2 ml of a secondary antibody at 1:2000 dilution for one hour. After washing, the beads were poured into a polystyrene petri dish and allowed to settle. The supernatant was removed and a solution of 5-bromo-4-chloro-3-indoyl phosphate and nitro blue tetrazolium was gently added as a substrate.

After incubation at room temperature for 15 minutes, the long v-mos beads turned purple in contrast to the short v-mos beads which remained colorless. This made it possible immediately to detect a single dark bead within a lawn of thousands of colorless beads. The distinction between the beads is illustrated in FIGS. 2 to 4, all of which are photographs at 40× magnification of the beads distributed in petri dishes. FIG. 2 shows a lawn of long v-mos beads labelled with the monoclonal antibody, FIG. 3 shows a mixture of long and short v-mos beads labelled with anti-v-mos monoclonal antibody, and FIG. 4 shows the ready detection of the single blue bead in a lawn of colorless beads. Accordingly, the beads that contained the peptide sequence of interest were readily distinguished and isolated from the other beads in the library.

After isolation, the Applied Biosystems 477A Protein Sequencer was employed to determine the N-terminal amino acid sequences of a single "long v-mos" resin bead.

8.3. CONCLUSION

This Example demonstrates the power of the instant invention to select a bead containing a bio-oligomer ligand, in this case a peptide, of interest from among a thousand-fold excess of non-binding, irrelevant beads. Furthermore, this Example demonstrates that a reactive bead may be isolated and the sequence of the peptide determined.

9. EXAMPLE

ISOLATION OF A SHORTER PEPTIDE LIGAND THAT BINDS TO A RECEPTOR MOLECULE

To further demonstrate the use of the method of the instant invention to isolate a particular peptide, a hexapeptide with the predetermined sequence Gly-Phe-Gly-Ser-Val-Tyr was synthesized on the standard 100 μm PAM resin using $N^\alpha$-Fmoc chemistry and other reagents from the standard solid phase peptide synthesis.

9.1. MATERIALS AND METHODS

Coupling reactions were performed as described in Section 8.1, supra. Alpha-amino-blocking groups were removed by 20% piperidine, the side chain protecting groups were removed by 50% TFA, and the peptide remained covalently linked to the polystyrene resin via a aminocaproic acid-β-alanine linker to yield a final structure Gly-Phe-Gly-Ser-Val-Tyr-aminocaproic acid-β-Ala-resin. This peptide sequence corresponds to residues 104 to 109 of the v-mos gene product described in Example 8, supra.

As in Example 8, anti-v-mos antibodies were collected from the hybridoma cell line producing mouse monoclonal antibody specific against this the v-mos peptide. The labelled secondary goat-anti-mouse IgG-alkaline phosphatase was obtained from Sigma.

9.2. RESULTS

Approximately 0.1 mg of the PAM resin/v-mos peptide described above was mixed with a hundred-fold excess of $N^\beta$-Fmoc-alanine PAM resin beads obtained from Bachem, Inc. Two ml of the purified monoclonal antibody (1 ug/ml) in PBS plus 0.1% Tween 20 were added to the peptide/ support mixture and incubated at room temperature for 45 minutes with gentle mixing.

The beads were washed on a small polypropylene disposable column (obtained from Isolab) which retained the beads on a frit. The beads were then mixed with 2 ml of alkaline phosphatase-labelled secondary antibody (1:100 dilution) for one hour. After washing, the beads were spread on a piece of glass filter and soaked in 2,2'-azinobis (3-ethylbenzthiozoline sulfonic acid) (ABTS) substrate with $H_2O_2$. After incubation at room temperature for 15 minutes, the PAM resin/v-mos peptide beads turned dark green. A small surrounding lighter green halo formed on the glass filter. The majority of the solid phase supports which lacked the v-mos peptide did not interact with the monoclonal antibody and therefore did not show any color change. The v-mos beads were readily distinguished.

9.3. CONCLUSION

This Example demonstrates that an acceptor molecule of interest will not react non-specifically with a solid phase support, but rather is specific for a solid phase support/ peptide combination. As in Example 8, supra, a positively reacting bead may be isolated, and the attached peptide sequenced.

10. EXAMPLE

DETERMINATION OF LIGANDS FOR STREPTAVIDIN AND ANTI-β-ENDORPHIN MAB

This Example further illustrates the very different approach to peptide ligand identification of the present invention. Instead of relying on a biologic system (e.g., the fusion filamentous phage) to generate a random library, the present methods effectively employ chemical synthesis of huge peptide libraries with each different peptide on an individual bead. Individual specific binding peptide beads are then physically isolated on the bead and the sequence of the attached peptide determined.

The approach depends on the ability to chemically synthesize a huge random peptide library and to couple it to an appropriate detection isolation, and structure determination system.

The means of eliminating this problem provided by the present invention is to separate the resin beads into a series of individual equal aliquots during each coupling cycle, and to allow each aliquot of resin to react to completion with an individual activated amino acid. After complete coupling, the various aliquots of resin are thoroughly mixed, washed, deprotected, washed, and again separated into aliquots for a new cycle of coupling. Accordingly, no one resin bead is exposed to more than one amino acid in any one coupling cycle and at the end of several such steps each bead will contain a single unique peptide sequence. The peptide library generated by this method will theoretically be truly random. Additionally, equimolar ratios of each peptide species will be obtained. The total number of permutations and hence number of peptides will depend on the number of aliquots and amino acids chosen in each coupling step, and the total number of coupling steps in the synthesis (length of the peptide).

The novel approach for simultaneously synthesizing a vast array of peptides not only provides a truly randomized and equimolar library, but more importantly, results in a library of solid phase peptide resin beads wherein each bead comprises only one unique peptide sequence. This last property is certain because during each cycle of peptide synthesis, each bead is in contact with only one individual amino acid at a time and each coupling reaction is driven to completion. The one bead-one peptide concept is in fact of primary importance in the success of the presently disclosed method.

With this synthetic approach in hand, virtually any peptide library can be synthesized with a well defined composition. For example, up to all 20 natural L-amino acids in individual aliquots can be used at every coupling step, or a single or a few amino acids can be used at certain coupling steps.

10.1. MATERIALS AND METHODS

10.1.1. SYNTHESIS OF A PEPTIDE LIBRARY

A large library with the structure X-X-X-X-X-β-Ala-aminocaproic acid-ethylenediamine-resin was synthesized (X=19 of the 20 common amino acids, all but cysteine, in each coupling step). The solid phase resin beads chosen for peptide synthesis were polydimethylacrylamide (PDA) (Milligen, Inc. U.S.A.).

The chemistry and the method of peptide synthesis with this resin were carried out according to Atherton and Sheppard (1988, Solid Phase Peptide Synthesis, A Practical Approach, IRL Press). Three grams of resin (approximately 2 million beads) were mixed gently with ethylenediamine overnight. After a thorough washing, aminocaproic acid, followed by β-alanine, were coupled to the resin using Fmoc chemistry, but without a cleavable linker. Randomization was carried out in the next five coupling steps, and all 19 Fmoc-amino acid-OPfp except cysteine were used separately during each coupling step. After the five coupling steps were completed, the Fmoc group was removed in 20% piperidine (v/v) in DMF. The side chain protecting groups removed with a mixture of 90% TFA (v/v), 1% anisole (v/v), and 0.9% ethanedithiol (v/v). The resin was neutralized with 10% diisopropylethylamine (in DMF) and stored in DMF at 4° C.

The linker β-alanine-aminocaproic acid-ethylenediamine consists of a total of 11 C atoms, and 4N atoms, with a maximum arm length of 17.6 A. Since 19 different amino acids were used at each of the five random coupling steps, the theoretical number of peptides was $19^5$, or 2,476,099 individual pentapeptides in this library.

As mentioned earlier, the general scheme of the methodology is to synthesize a huge library of random peptides on individual solid phase resin beads such that each resin bead contains a single peptide species. An individual resin bead that interacts with an acceptor molecule can then be identified, physically isolated, and the amino acid sequence of the peptide ligan will then be determined by Edman degradation. The success of the methodology, therefore, requires precise identification of a peptide sequence on a single bead. Using an automatic protein sequencer (Model 477A-01 Pulsed Liquid Automatic Protein/Peptide Sequencer, Applied Biosystems, Foster City, Calif.), 50–500 pmole of peptides were routinely recovered from each resin bead. Furthermore, preview analysis (MiMarch et al., 1990, "Peptides: Chemistry, Structure and Biology," Proceedings of the Eleventh American Peptide Symposium, Jul. 9–14, 1988, La Jolla, Calif., ESCOM, Leiden, pp. 229–230) of the sequencing data showed that the coupling efficiency of the solid phase peptide synthesis was in excess of 98%.

10.1.2. SPECIFIC IDENTIFICATION AND SELECTION OF PEPTIDE LIGANDS FROM THE LIBRARY

Identification and selection of specific peptide ligands from the random library can easily be accomplished with immunological techniques, such as an Enzyme Linked Immunoabsorbant Assay (ELISA), immunofluorescence or with immunomagnetic beads. For the experiments described herein, immunohistochemical techniques were used in the detection system. The specific-binding acceptor molecules used in this study were (i) the biotin-binding protein streptavidin, and (ii) an anti-β-endorphin monoclonal antibody (MAb). Using the fusion filamentous phage epitope library system (Cwirla et al; Devlin et al., Section 2 supra), peptide ligands have been successfully identified with both of these acceptor molecules.

The immunohistochemical techniques were used for the detection of streptavidin binding-beads. The random library of peptide beads were gently mixed with incrementally increasing double distilled water to dilute the DMF. Subsequently, the beads were washed thoroughly with PBS, and gelatin (0.1% w/v) was used to block any nonspecific binding. A 1:200,000 dilution of streptavidin-alkaline phosphatase (Pierce, Rockford, Ill.) was then added to the beads with gentle mixing for one hour. The beads were then thoroughly washed, and the standard substrate 5-bromo-4-chloro-3-indolyl phosphate/nitro blue tetrazolium (BCIP/NBT) was added. The beads together with substrate solution were transferred into 15 polystyrene petri dishes (100×20 nm), and the reaction was carried out for up to two hours. The beads with bound streptavidin-alkaline phosphatase turned dark blue, while the majority of the beads in the library remained colorless.

10.1.3. DETERMINATION OF PEPTIDE LIGAND AFFINITIES

Peptide ligand binding affinities for the anti-β-endorphin monoclonal antibody were determined in solution phase. The anti-β-endorphin binding assay measured peptide ligand inhibition of 5.0 nM [$^3$H][Leu]enkephalin (specific activity=39.0 Ci/mmole, New England Nuclear, Boston, Mass.) binding to 125–200 ng/ml anti-β-endorphin MAb in 1.0 ml of 40 mM Tris-HCl, 150 mM NaCl, pH 7.4 buffer containing 1.0 mg/ml bovine serum albumin, 0.1% (v/v) Tween 20, and 0.05% (w/v) sodium azide. Specific binding was defined as the difference between binding measured in the presence or absence of 1.0 μM unlabelled [Leu] enkephalin. Bound radioligand was precipitated by the addition of a 10-fold excess of Protein-G Sepharose (Pharmacia) followed by an overnight incubation (23°–24° C.). The Protein-G Sepharose was collected by centrifugation (13,000×g for 5 minutes) and the pellets suspended in 250 μl 5% (v/v) acetic acid before transfer to vials for liquid scintillation counting. $K_d$ values (n=3) were determined by saturation analysis using 5 radioligand concentrations (1.87–30 nM) for [$^3$H][Leu]enkephalin with duplicate total and nonspecific binding samples for each. The average $K_d$ value measured was 9.79±4.63 nM. Peptide ligand inhibition curves were produced for eight concentrations of the peptide over a 400-fold range. Binding data for saturation and inhibition studies were analyzed by weighted-nonlinear regression methods using appropriate one site models reported by Knapp et al. (1990, J. Pharmacol. Exp. Ther. 255:1278–1282). Ki values for inhibition binding constants were calculated using the method of Cheng and Prusoff (1973, Biochem. Pharmacol. 22:3099–3102). Each Ki value was calculated from three to four independent determinations.

10.2. RESULTS

A large synthetic random peptide library (X-X-X-X-X-resin, where X= the 19 common amino acids (cysteine was not used) for a total of $19^5$=2,476,099 permutations) was screened. Approximately 2 million beads were present in the portion of the library screened. In a first-stage screen with streptavidin-alkaline phosphatase alone (See Section 10.1.2, supra), approximately 75 beads were stained with various color intensities and were physically selected and removed under a dissecting microscope with the aid of a micromanipulator. Each bead was then washed in 8M guanidine hydrochloride to remove the bound streptavidin enzyme conjugate. Subsequently, each bead was individually loaded onto a glass filter for an Applied Biosystem Protein Sequencer (ABI) cartridge. The sequences of 28 of the 75 beads are shown in Table 1. All these beads have consensus sequence of either HPQ or HPM. The photomicrograph in FIG. 5 illustrates how a positive (dark blue) bead can easily be identified in a background of many thousands of negative (colorless) beads during the peptide ligand library screening.

TABLE 1

Peptide Sequences of Individual Beads that Interact with Streptavidin[a]

| | | |
|---|---|---|
| HPQFV ([b]0.8, [c]1120) | GHPQG (0.44, 250) | PLHPQ (2.5, 48) |
| HPQGP (0.35, 60) | MYHPQ | AIHPQ |
| HPQAG (1.5, 53) | REHPQ (0.56, 112) | AAHPQ (0.9, 476) |
| LHPQF (0.47, 286) | IQHPQ (1.8, 192) | [d]TPHPQ (0, 158) |
| FHPQG (0.23, 72) | GNHPQ (0, 222) | WNHPM (2.5, 59) |
| GHPQN (0.5, 44) | TVHPQ (0, 96) | WTHPM (1.4, 202) |
| THPQN (0.5, 44) | IGHPQ | VHPMA (0.6, 21) |
| QHPQG (2.3, 60) | WMHPQ (2.7, 257) | [d]MHPMA (0.31, 140) |
| IHPQG (2.1, 57) | GAHPQ | |

[a]These ligands were identified by screening a 2,476,099 ($19^5$) peptide library.
[b]The first number in parenthesis indicated the percentage of preview for cycle 5 of Edman degradation (i.e., quantity of residue 5 of cycle 4/quantity of residue 5 of cycle 5).
[c]The second number in parenthesis indicated the amount of peptide (pmol) recovered during the sequencing.
[d]Two TPHPQ and two MHPMA sequences were identified; no other repeats were detected.

To prove that the HPQ consensus sequences actually bind to the biotin-binding site in the streptavidin molecule, LHPQF-β-Ala-aminocaproic acid-ethylenediamine-resin (LHPQF-resin) was synthesized. The LHPQF-resin was then mixed with streptavidin-alkaline phosphatase in the presence of varying concentration of biotin. The results are shown in FIG. 6. Biotin at 100 nM completely blocked staining of the LHPQF-resin. At 10 and 1.0 nM, biotin partially inhibited the staining, and at 0.1 nM concentration, it had no effect on the staining of the LHPQF-resin by streptavidin-alkaline phosphatase. The inhibition study establishes that the HPQ consensus sequence binds to the biotin-binding site of streptavidin.

Prior to using the same random peptide library to screen with anti-β-endorphin MAb, all the blue beads that had stained for streptavidin-alkaline phosphatase alone were removed. The remaining beads were then treated with 8M guanidine hydrochloride to remove any bound protein. This recycled library was then mixed with biotinylated anti-β-endorphin MAb (anti-β-endorphin, clone 3-E7, was obtained commercially from Boehringer Mannheim, Indianapolis, Ind.) for 16 hours. After extensive washing, a secondary step with streptavidin-alkaline phosphatase was used to trigger the staining reaction for the ELISA. Six peptides with consensus sequence that have close resemblance to the native ligand, Leu-enkaphalin (YGGFL), were identified in this screening: YGGMV, YGALQ, YGGLS, YGGFA, YGGFT and YGGFQ. Peptide analogues with various carboxyl terminus of these ligand leads were synthesized and their affinity (Ki) was determined using [$^3$H] Leu-enkaphalin (New England Nuclear, Boston, Mass.) as the labelled ligand and the unlabelled peptides as the competing ligand (anti-β-endorphin assay, Section 10.1.2, supra). The results of these studies are summarized in Table 2.

TABLE 2

Affinity of the Peptide Ligands to Anti-β Endorphin Monoclonal Antibody

| Peptide | Ki, nM Carboxyl Terminus | | | |
|---|---|---|---|---|
| | —OH | —NH$_2$ | -βA—OH | -βA—NH$_2$ |
| [a]YGGFL | 17.5 ± 3.2 | 27.9 ± 2.3 | 17.1 ± 1.8 | 13.7 ± 1.7 |
| YGGFA | 32.9 ± 2.0 | 72.0 ± 16.4 | 82.3 ± 8.8 | 93.6 ± 34.7 |
| YGGFT | 36.9 ± 7.7 | 65.2 ± 16.8 | 50.6 ± 8.9 | 43.3 ± 2.3 |
| YGGFQ | 15.0 ± 1.7 | 40.1 ± 6.0 | 39.4 ± 2.3 | 45.4 ± 11.6 |
| YGGLS | 726 ± 134 | 991 ± 52 | 916 ± 182 | 1150 ± 247 |
| YGGLQ | 1980 ± 303 | 2910 ± 695 | 1470 ± 120 | 1910 ± 504 |
| YGGMV | 8780 ± 1500 | 14000 ± 1110 | 5140 ± 885 | 7160 ± 1010 |

[a]YGGL is [Leu$^5$]enkaphalin, the native ligand for the anti-β-endorphin MAb.

10.3. DISCUSSION

The ability to synthesize individual peptides on each bead combined with a sensitive and specific detection and selection system is the key to success with the methodology of the present invention. This new methodology is termed the "selectide process". An individual peptide bead selected from the library and treated with 8M guanidine hydrochloride (to remove bound protein) has been effectively purified, with the peptide remaining covalently linked to the resin and ready for sequencing. State of the art automatic peptide sequencers are capable of sequencing a peptide at concentrations as low as 5–10 pmole. Furthermore, the blue stain that irreversibly binds to the bead does not interfere with sequencing. During each coupling cycle of randomization, every effort was made to optimize the synthetic methodology, including use of large excesses of N$^α$-Fmoc-amino acids. The preview analysis of the sequencing raw data clearly demonstrated that the coupling-efficiency of the synthetic chemical reactions exceeded 98%.

Since the stained beads stand out conspicuously in a background of colorless beads (e.g., FIG. 7), it is almost effortless to screen visually 2 million beads under a dissecting microscope in a series of 10–15 petri dishes and select out reactive beads for sequencing. Furthermore, we can estimate the relative affinity of various ligands by examining the relative staining intensity of each positive bead. This property enables us to choose beads of specific color intensity for sequencing.

Devlin et al. (1990, Science 259:404–406, Section 2., supra) reported the importance of HPQ, HPM, and HPN sequences in their 20 streptavidin binding ligands isolated with the fusion filamentous phage technique. Of their 20 isolates, 15 had HPQ, 4 had HPM, and 1 had HPN consensus sequences. Interestingly, the peptide library yielded 28 different peptides, 23 of which have an HPQ consensus sequence and 5 of which have an HPM consensus sequence (Table 1). It appears that the position of the HPQ/HPM sequence in the pentapeptide was not important for streptavidin-binding. Of all the HPQ or HPM pentapeptide sequences identified, only two were repeated (TPHPQ and MHPMA). This is in sharp contrast to the data reported by Devlin et al., supra, where there were multiple repeats among their 20 isolates suggesting that selection bias occurred in their biosynthetic method.

In the anti-β endorphin system, 6 peptides with sequences very similar to that of the native ligand YGGFL were identified (Table 2). These results are similar to those obtained with the fusion filamentous phage technique, to which used the same monoclonal antibody (clone 3-E7) (Cwirla, et al., 1990, Proc. Natl. Acad. Sci U.S.A. 87:6378–6382, supra). Although the peptide library yielded fewer ligand sequences than were obtained by Cwirla et al., 50% of the ligands obtained had much higher affinity for the antibody than any of those selected with the phage technique.

11. EXAMPLE

A LIMITED PEPTIDE LIBRARY

In another set of experiments, the present invention was tested with another antibody system wherein the epitope was located in the middle of the peptide chain rather than at its N-terminus (as in the case of the β-endorphin). The antibody used was an anti-v-mos peptide monoclonal antibody (anti-v-mos MAb) (See Section 11.1, infra). This antibody was provided by immunizing mice with a 12 amino acid peptide (LGSGGFGSVYKA) corresponding to residues 100 to 111 of the v-mos oncogene product. The peptide was conjugated to a carrier protein prior to immunization. In ELISA testing, this anti-v-mos MAb detects homologous sequence of v-mos, MOS, neu/HER-1, and HER-2 gene products.

11.1. MATERIALS AND METHODS

Using a commercially available multi-pin system (Geysen et al., 1986, Mol. Immunol. 23:709–715) epitope mapping kit (Cambridge Research Biochemical, Boston) to synthesize overlapping peptides (sets of tetrapeptides, pentapeptides, and hexapeptides), the epitope within the 12 amino acid v-mos. peptide recognized by the anti-v-mos MAb was mapped to the pentapeptide sequence (FGSVY) (i.e., residue 6–10 of the v-mos dodecapeptide).

In the present experiment a restricted random library was used in which the amino acids valine and serine that are present in the v-mos epitope were purposely omitted. This restricted random library has the following composition: G-X-X-X-X-X-β-Ala-aminocaproic acid-ethylenediamine-resin, wherein X=Glu, Pro, Asn, Phe, His, Thr, Lys, Leu, Gly, Tyr, Ala, Met, Arg, Trp. These 14 amino acids were chosen so that both valine and serine were omitted, and yet all the side chain functional groups were still included, that is (i) Asn was selected but not Gln; (ii) Glu was selected but not Asp; (iii) Thr was selected but not Ser; (iv) Leu was selected but not Ile or Val; and (v) Met was selected but not Cys. Since 14 amino acids were chosen at each of the five random coupling steps, the theoretical number of peptides was 14$^5$, or 537,824 individual peptides.

The hybridoma cell line that produces anti-v-mos monoclonal antibody was purchased from Microbiological Associates Inc., Maryland (Hybridoma No. 165-28E7, SCRF 354, Lot No. 165–119).

Peptide ligand affinity for anti-v-mos mAb was measured by solution phase binding studies using [$^3$H]acetyl v-mos peptide ([$^3$H]Ac-v-mos) as the radioligand. The radioligand was prepared by N-terminal acetylation of v-mos peptide, prior to the deprotection of the side chains, with an equimolar amount of [$^3$H]sodium acetate (specific activity=2.52

Ci/mmole, New England Nuclear, Boston, Mass.). The [³H]Ac-v-mos product, which was separated from unreacted v-mos peptide with reverse phase HPLC, had a specific activity of 2.50 Ci/mmole. The binding affinity of [³H]Ac-v-mos for anti-v-mos MAb (=10 μg/ml) was measured in 1.0 ml PBS-gelatin buffer (0.05% gelatin in PBS) at 23°–24° C. after a three hour incubation. Specific binding was defined as the difference between [³H]Ac-v-mos binding in-the presence (nonspecific) and absence (total) of 100 μM unlabelled v-mos peptide for each [³H]Ac-v-mos concentration. Bound radioligand was separated by centrifugation using a 10-fold excess (binding capacity relative to immunoglobulin used) of Protein-G Sepharose (Pharmacia) to precipitate the antibody. Saturation binding analysis from five determinations over a concentration range of 125–5000 nM showed that [³H]Ac-v-mos was bound to anti-v-mos mAb with a Kd value of 850±160 nM. The binding affinities of the peptide ligands were determined with binding inhibition studies using seven peptide ligand concentrations in competition for 10 μg/ml anti-v-mos MAb with 20 nM [³H]Ac-v-mos with the conditions as described above. Over 50% of the total binding was specific in the inhibition studies. Saturation and inhibition binding constants were determined for single site binding by nonlinear regression analysis as previously described (Knapp and Yamamura, 1990, Life Sci. 46:1457–1463).

11.2. RESULTS

Approximately 230,000 beads were screened with an anti-v-mos alkaline phosphatase conjugate. Therefore, less than 43 percent of permutations were examined. After incubation with the substrate, about 50 of the beads stained intensely blue. Twenty-four of these beads were physically selected out and the amino acid sequence of eleven of them was determined. Additionally, seventeen colorless beads were randomly picked for sequencing.

The anti-v-mos ligand sequencing results are shown in Table 3. Since both valine and serine were purposely not included in this peptide library, it is not surprising to see that none of the 11 peptide ligand sequences resemble the native epitope (FGSVY). Although there were no repeats in the 11 peptide ligands, their sequences were non-random. Both arginine and tyrosine occur frequently in these sequences. Furthermore, at least one and sometimes two arginines are present at the second and/or third position of each of these peptide ligands. On the other hand, the negative beads selected randomly did not shown any common amino acid sequence pattern. Although the sample size is limited, the chi-square goodness of fit statistic for the sequences from the negative beads was not significant ($x^2$=18.27, df=13, P=0.15) indicating that we have no evidence for a non-uniform distribution of amino acids for the non-staining random peptide beads.

TABLE 3

Peptide Sequence of Individual Beads that
Interact with Anti-v-mos Monoclonal Antibody A. Interactive Beads
| | |
|---|---|
| GRRGME | GRYMPK |
| GRRPYG | GFRHMA |
| GRRAYE | GFRYHN |
| GRREGP | GHRYFH |
| GRYAKH | GWREKE |
| GRKTYY | |

B. Non-interactive Beads

TABLE 3-continued

Peptide Sequence of Individual Beads that
Interact with Anti-v-mos Monoclonal Antibody

| | |
|---|---|
| GKELAG | GFEKHP |
| GPYLMW | GWGAYP |
| GTKMNF | GAARPP |
| GEKMEF | GLFGME |
| GYEEPK | GRLNTL |
| GKKPNP | GMTHAY |
| GEYAPP | GPYGMA |
| GGFMEF | GHYNNL |
| GPKFMA | |

Some of the positive ligands were synthesized and their affinity for the anti-v-mos MAb were determined with solution phase binding studies (Section 11.1, supra). The result of these studies are summarized in Table 4. Table 4A summarizes the binding affinities of the v-mos epitope (as determined by epitope mapping) for anti-v-mos monoclonal antibody. The effect of altering the carboxyl terminus is also shown. Table 4B summarizes the binding affinities of mimotopes identified from a peptide library that lacks several of the amino acids in the v-mos epitope. β-Alanine amide was included in some of the ligands tested to simulate the structure of the identified ligand to which the antibody binds on the bead.

TABLE 4

Binding Affinity of Peptide Ligand for Anti-v-mos MAb

| Peptide | Ki, μM |
|---|---|
| A. LGSGGFGSVYKA (v-mos peptide) | 3.2 ± 0.4 |
| GFGSVY—NH₂ (v-mos epitope) | 246–337 |
| GFGSVY—OH | >1000 |
| GFGSVY-βA—NH₂ | 409–442 |
| GFGSVY-βA—OH | 529–770 |
| B. GRRAYE—OH | 6.79 ± 2.31 |
| GRRAYE—NH₂ | 24.70 ± 7.00 |
| GRRAYE-βA—OH | 15.10 ± 0.50 |
| GRRAYE-βA—NH₂ | 9.02–20.40 |
| GRRGME—OH | >100 |
| GRRGME-βA—NH₂ | 24.00 ± 8.40 |
| GRREGP-βA—NH₂ | 26.90 ± 6.20 |
| GRRPYG—OH | >1000 |
| GRRPYG-βA—NH₂ | 20.50 ± 4.50 |

The affinity of the best anti-v-mos mimotope in Table 4 is approximately 2.5 fold less than that of the native peptide. Although none of the peptide ligands tested have the a Ki value as low as the native v-mos ligand, the results clearly demonstrate that by using a random library lacking some of the amino acids present in the native epitope, a series of structurally different mimotopes with affinity for the acceptor molecule, i.e., anti-v-mos MAb, can be identified.

11.3. DISCUSSION

The anti-v-mos MAb used in this study had a relatively low affinity to the v-mos peptide (the immunogen). Serine and valine were presented in the v-mos linear epitope (FGSVY) but were purposely omitted from the screening library used; nonetheless the method permitted definition of a linear mimotope of totally different sequence and amino acid composition, but with comparable affinity for the antibody. This clearly illustrates the complexity as well as versatility of macromolecular-peptide interactions.

12. EXAMPLE

A SELECTIVELY CLEAVABLE LINKER: ONb

A set of four peptides incorporating the UV-cleavable linker ONb (see Section 5.4, supra) were prepared and tested.

12.1. MATERIALS AND METHODS

The following four peptides were prepared on two resins using standard solid phase synthesis techniques (e.g., Sections 6 and 7, supra):

i) Fmoc-Trp-Tyr (OBu$^t$)-Phe-βNb-gAla-ACA-EDA-PepSyn K ii) TRP-Tyr-Phe-ONb-βAla-ACA-EDA-PepSyn K iii) Fmoc-Typ-Tyr (OBu$^t$)-Phe-ONb-βAla-ACA-4-MBHA iv) Trp-Tyr-Phe-ONb-βAla-ACA-4-MBHA Each peptide was irradiated for 1 and 3 hours with ultraviolet (UV) and visible (VIS) light in 0.3 ml of water or 3/7 mixture of chloroethanol:dichloromethane. A total of 16+16 experiments were run and assayed.

After exposure the supernatant was filtered off, lyophilized and re-dissolved to equal volumes of MeOH (0.3 ml). The products were analyzed on the HPLC.

12.2. RESULTS

Analysis by HPLC clearly showed no tripeptide release upon VIS irradiation in water, and almost complete release of tripeptide upon UV irradiation for one hour, In particular, peptide i in water was cleaved to a single product. In some cases, two products were observed to elute from HPLC. At longer exposure times (UV), interconversion between the two products was observed in at least a few cases.

12.3. DISCUSSION

The UV-sensitive linker clearly works to release peptide in aqueous solution. Exposure times 1 hour would be suitable to get incomplete peptide release. The results also show that polyamide resin is stable to and compatible with aqueous systems.

13. EXAMPLE

IDENTIFICATION OF AN ENZYME MIMIC

13.1. MATERIALS AND METHODS

A random library of pentapeptides comprising 19 of the 20 common amino acids (excluding cysteine) was prepared according to the instant invention (see Section 10.1, supra).

The peptide library was exposed to the chromogenic substrate nitro blue tetrazolium (NBT) chloride in the absence of exogeneous enzyme under conditions conducive to product formation, and positive reacting beads were identified. These beads were selected and sequenced.

13.2. RESULTS

The sequences of five beads that appeared to catalyze the reduction of NTB to its dark blue diformazan product are shown in Table 5.

TABLE 5

| Sequence Of Peptide-Beads That Appear To Act As Enzymes |
|---|
| PNNNH |
| WNNNM |
| PNNNG |
| MNNNR |
| QNNNR |

13.3. DISCUSSION

The foregoing results suggest that the peptide PNNNH-bead is capable of reducing NBT to a dark blue diformazan pigment either chemically or enzymatically. As such, the peptide or peptide-bead demonstrates activity as an "artificial enzyme" or enzyme mimic.

14. EXAMPLE

SCREENING FOR AN ANTI-CANCER PEPTIDE SEQUENCE

A limited library comprising pentapeptides with the composition tyrosine followed by a random sequence comprising five amino acids selected from the group of amino acids consisting of glutamic acid, serine, valine, glycine, arginine and asparagine contains peptide sequences with anti-cancer (i.e., anti-tumor) cell line activity.

14.1. MATERIALS AND METHODS

A random peptide library of this invention was synthesized with a hydrolyzable diketopiperazine linker. 96-well plates were used in screening for anti-cancer (anti-tumor cell) drugs.

After deprotection of the side chain protecting group and the N$^α$-Fmoc group, the peptide bead library was neutralized with DIEA (diisopropyl ethylamine) and washed extensively with DMF to remove any residual potentially toxic chemicals. The library was then exchanged gradually into 0.01M HCl (condition where the linker is stable) and finally washed with 0.001M HCl. Approximately 10 library beads were then transferred into each well of a plate. Fifty $\mu$l RPMI medium (with 25 mM HEPES buffer) were then added to each well to neutralize the solution pH. At neutral or slightly alkaline pH, the peptides will be released (e.g., after 16–24 hours).

Either (1) a portion or the whole amount of medium is transferred into a separate plate with a specific cancer cell line, or (2) the cancer cell line is added directly into the well with the beads. Approximately 2500 lung cancer cells/well were used. The plates were then incubated at 37° for 7 days and an MTT assay was performed to quantitate the relative cytotoxicity of released peptides in each well.

Various established human carcinoma, lymphoma, myeloma, as well as leukemia cell lines can be used for the screening. Examples are the NCI panel tumors: L1210 lymphoid leukemia; B16 melanoma; Lewis lung carcinoma; M5076 sarcoma; colon 38 carcinoma; and MX-1 human breast carcinoma. Other examples are: MCF-7 breast cancer; 8226 myeloma cell line; P388 (mouse) leukemia cell line; and the Hawkins non-small cell lung cancer line.

14.2. RESULTS

A library comprising about 8000 peptides with the sequence YXXXXX-[bead], wherein Y is Tyr, and X Ss Glu, Ser, Val, Gly, Arg, or Asn, was screened. In two experiments, 3-4 supernatants containing released peptide out of a few thousand demonstrated growth inhibition of the Hawkins non-small cell lung cancer line. As each well contained approximately 10 beads, substantially all of the 8,000 possible sequences were tested and as many as 3 active peptide beads identified. The same type of result was seen with both direct incubation of beads with cells and with transfer of the released peptide supernatant.

14.3. DISCUSSION

These results indicate that a limited library of peptides can include some peptide sequences with cytotoxic activity. In the foregoing example, approximately 0.05% of the possible sequences demonstrated anti-cancer cell activity. By assaying supernatants containing released peptide in multiple assays, toxicity against other cancer cells and against normal tissue cells can be determined.

In this way peptide sequences with broad toxicity for tumor cells or with toxicity for a specific tumor cell line can be identified; those sequences with low toxicity for normal cells would be preferred as therapeutic agents. This method can be applied to screening antimicrobial, antiparasitic and growth factor antagonists.

A similar screening approach for a growth factor agonist uses a growth-factor dependant cell line. In such an assay, peptide sequences with growth factor agonist activity will stimulate growth of cells cultured in the absence of the essential growth factor.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for determining the chemical structure of a bio-oligomer ligand for an acceptor molecule comprising the steps of:
   (a) introducing to a library of bio-oligomers attached to solid phase supports wherein each solid chase support is attached to a single wholly deprotected bio-oligomer species, an acceptor molecule of interest such that said acceptor molecule will recognize and bind to one or more solid phase support/bio-oligomer species within the library;
   (b) isolating a solid phase support/bio-oligomer combination that exhibits binding with the acceptor molecule; and
   (c) determining the chemical structure of the bio-oligomer of the solid phase support/bio-oligomer isolated in step (b).

2. The method of claim 1 in which the acceptor molecule is selected from the group consisting of antibodies, receptors, viruses, bacteria, proteins, carbohydrates, nucleic acids, lipids, drugs, metals and small molecules.

3. The method according to claim 2 in which the acceptor molecule is an antibody.

4. The method according to claim 2 in which the acceptor molecule is a receptor.

5. A method for determining the chemical structure of a biologically active bio-oligomer ligand comprising the steps of:
   (a) subdividing a bio-oligomer library comprising a multiplicity of solid phase supports, wherein a single deprotected bio-oligomer species is attached to each solid phase support, and in which the library is prepared by a method comprising repeating k times, wherein k is at least three, the steps of:
      (i) providing at least two aliquots of a solid phase support, in which the solid phase support comprises a linker selected from the group consisting of a selectively cleavable linker, a plurality of selectively cleavable linkers, or a combination of a non-cleavable linker and a selectively cleavable linker, by means of which the bio-oligomer can be attached covalently;
      (ii) separately introducing a species of subunits of the bio-oligomers to each of the aliquots of solid phase supports such that a different subunit is introduced to each aliquot, at least one of said subunits having a protecting group or a plurality of protecting groups;
      (iii) completely covalently coupling the subunit to the reactive sites of the solid phase support;
      (iv) thoroughly mixing and deprotecting the aliquots of the solid phase supports whereby a reactive site is provided; and, after repeating steps (ii) through (iv) k times, a final step of removing any protecting groups such that the deprotected bio-oligomer remains covalently attached to the solid phase supports in which the solid phase support is modified so that a portion of bio-oligomer can be released;
   (b) releasing a portion of the bio-oligomers from the solid phase support/bio-oligomer by cleavage of a clearable linker;
   (c) detecting the biological activity of the released bio-oligomer interest in situ;
   (d) isolating a solid phase support/bio-oligomer combination that exhibits the specific biological activity of interest; and
   (e) determining the chemical structure of the bio-oligomer remaining on the solid phase support/bio-oligomer isolated in step (d).

6. The method according to claim 5 in which the solid support is modified to be acid-sensitive, base-sensitive, nucleophilic-sensitive, photosensitive, electrophilic-sensitive, oxidation-sensitive, or reduction-sensitive.

7. The method according to claim 5 in which the solid phase support comprises a linker which is acid-sensitive, base-sensitive, nucleophilic-sensitive, electrophilic-sensitive, photosensitive, oxidation-sensitive, or reduction-sensitive.

8. The method according to claim 5 in which the in situ release of step (b) is affected by enzymatic cleavage, chemical clevage or a photochemical cleavage.

9. The method according to claim 5 in which the detection of step (c) is of a biological activity selected from the group consisting of cytotoxicity, antitumor activity, antibacterial activity, antiviral activity, antifungal activity, anti-parasite activity, growth factor activity, growth inhibitory activity, hormone activity, neurotransmitter activity, immunomodulator activity and regulatory activity.

10. A method for determining the chemical structure of a bio-oligomer which inhibits an enzyme catalyzed reaction comprising:
   (a) generating a bio-oligomer library of claim 1 in which the solid phase support is modified;
   (b) releasing a portion of the bio-oligomers from the solid phase support/bio-oligomer combination in situ;
   (c) detecting inhibition of the enzyme catalyzed reaction of interest in situ;

(d) isolating a solid phase support/bio-oligomer combination detected in step (c);

(e) determining the chemical structure of the bio-oligomer remaining on the solid phase support/bio-oligomer isolated in step (d).

11. A method for determining the chemical structure of a bio-oligomer ligand for an acceptor molecule comprising the steps of:

(a) introducing, to a bio-oligomer library comprising a multiplicity of solid phase supports, wherein a single deprotected bio-oligomer species is attached to each solid phase support, and which the library is prepared by a method comprising repeating k times, wherein k is at least three, the steps of:

(i) providing at least two aliquots of a solid phase support said supports having a reactive site to which a species of subunit of the bio-oligomer can be covalently coupled;

(ii) separately introducing a species of subunits of the bio-oligomers to each of the aliquots of solid phase supports such that a different subunit is introduced to each aliquot, at least one of said subunits having a protecting group or a plurality of protecting groups;

(iii) completely covalently coupling the subunit to the reactive sites of the solid phase support;

(iv) thoroughly mixing and deprotecting the aliquots of the solid phase supports whereby a reactive site is provided; and, after repeating steps (ii) through (iv) k times, a final step of removing any protecting groups such that the deprotected bio-oligomer remains covalently attached to the solid phase supports, an acceptor molecule of interest such that said acceptor molecule will recognize and bind to one or more solid phase support/bio-oligomer species within the library;

(b) isolating a solid phase support/bio-oligomer combination that exhibits binding with the acceptor molecule; and (c) determining the chemical structure of the bio-oligomer of the solid phase support/bio-oligomer isolated in step (b).

12. The method according to claim 1, 5, 10, or 11 in which the subunits are selected from the group consisting of amino acids, amino acid analogs, and peptidomimetics.

13. The method according to claim 1, 5, 10, or 11 in which the subunits are linked by a bond selected from the group consisting of amide, ester, ether bonds and combinations thereof.

* * * * *